(12) United States Patent
Dekker et al.

(10) Patent No.: US 6,630,179 B1
(45) Date of Patent: Oct. 7, 2003

(54) OXIHUMIC ACID AND ITS USE IN THE TREATMENT OF VARIOUS CONDITIONS

(75) Inventors: Johannes Dekker, Faerie Glen (ZA); Constance Elizabeth Medlen, Rietondale (ZA)

(73) Assignee: Enerkom (Proprietary) Limited, Pretoria (ZA)

( * ) Notice: Subject to any disclaimer, the term of this patent is extended or adjusted under 35 U.S.C. 154(b) by 0 days.

(21) Appl. No.: 09/787,876

(22) PCT Filed: Sep. 22, 1999

(86) PCT No.: PCT/IB99/01569
§ 371 (c)(1),
(2), (4) Date: Jun. 20, 2001

(87) PCT Pub. No.: WO00/16786
PCT Pub. Date: Mar. 30, 2000

(30) Foreign Application Priority Data

Sep. 23, 1998 (ZA) ............................... 98/8731
Mar. 10, 1999 (ZA) ............................... 99/1926

(51) Int. Cl.[7] ...................... A61K 35/78; A61K 31/235; A01N 25/00
(52) U.S. Cl. .................. 424/762; 514/533; 514/885
(58) Field of Search .................. 424/762; 514/885, 514/533

(56) References Cited

U.S. PATENT DOCUMENTS

| 4,912,256 A | * | 3/1990 | Cronje |
| 4,999,202 A | * | 3/1991 | Cronje |
| 5,543,300 A | * | 8/1996 | Inglot |
| 5,747,050 A | * | 5/1998 | Tolpa et al. |
| 5,876,966 A | * | 3/1999 | Reed |
| 5,945,446 A | * | 8/1999 | Laub |

FOREIGN PATENT DOCUMENTS

| GB | A2215603 | 9/1989 |
| WO | A1-9216216 | 10/1992 |
| WO | A1-9508335 | 3/1995 |
| WO | A1-9834629 | 8/1998 |

OTHER PUBLICATIONS

Ye et al., Database Biosis Online, XP002131261, (1985).
Amosova et al., Database Embase Online, XP002131262 (1990).
Inglot et al., Archivum Immunologae et Therapiae Experimentals, vol. 41, No. pp. 73–80 (1993).
Adamek, Proceedings of the 5th Int'l Peat Congress, vol. 1, 21–25, pp. 417–429 (1976).
Mesrogli et al., Zentralblatt Fur Gynakologie, vol. 113, No. 10, pp. 583–590, (1991).

* cited by examiner

Primary Examiner—Samuel Barts
Assistant Examiner—Paul A. Zucker
(74) Attorney, Agent, or Firm—Birch, Stewart, Kolasch & Birch, LLP

(57) ABSTRACT

A pharmaceutical composition comprising an oxihumic acid, salt, ester, or derivative thereof as an active ingredient is disclosed. The composition is preferably administered only for stimulating lymphocytes in a human, animal, or bird. It may be used in treating viral and bacterial infections, HIV infections, opportunistic diseases, inflammation, pain and fever, cancer growth, and diseases associated with viral infection and a depressed immune system.

9 Claims, 30 Drawing Sheets

Effects of oxihumate on resting and PHA-stimulated, monocyte depleted, human lymphocyte cultures Effects of oxihumate on resting and PHA-stimulated, monocyte depleted, human lymphocyte cultures Comparative results of synthetic humic acid and oxihumate on resting and PHA-stimulated, monocyte depleted human lymphocyte cultures.

Effect of oxihumate on interleukin 2 production by stimulated human lymphocytes

Effect of oxihumate and of oxihumate-treated human lymphocytes on the survival of a human liver cancer cell line (PLC)

Weights of HIV-positive patients on a 2-week treatment of either placebo, 2 g, 4 g or 6 g oxihumate, measured every 5 days and expressed as a percentage of their average weight before treatment Effect of a 2 week treatment of HIV-positive individuals with oxihumate on serum sodium and potasium levels Effect of a 2 week treatment of HIV-positive individuals with oxihumate on plasma glucose levels Effect of a 2 week treatment of HIV-positive individuals with oxihumate on serum L-alanine transferase and aspertate amino transferase levels Effect of a 2 week treatment of HIV-positive individuals with oxihumate on serum urea and creatinine levels Effect of a 2 week treatment of HIV-positive individuals with oxihumate on haemoglobin levels Effect of a 2 week treatment of HIV-positive individuals with oxihumate on platelet counts Effect of a 2 week treatment of HIV-positive individuals with oxihumate on absolute neutrophil counts Effect of a 2 week treatment of HIV-positive individuals with oxihumate on viral load Effect of a 2 week treatment of HIV-positive individuals with oxihumate on absolute lymphocyte counts Effect of a 2 week treatment of HIV-positive individuals with oxihumate on CD4 counts Effects of a two-week treatment of HIV-positive patients with oxihumate on PHA-stimulated lymphocyte transformation *in vitro*

OXIHUMIC ACID AND ITS USE IN THE TREATMENT OF VARIOUS CONDITIONS

This application is the national phase under 35 U.S.C. §371 of PCT International Application No. PCT/IB99/01569 which has an International filing date of Sep. 22, 1999, which designated the U.S.A.

BACKGROUND OF THE INVENTION

This invention relates to oxihumic acid and its use in the treatment of various conditions.

Humic acids are formed during the decomposition of organic matter and can therefore be found in practically all natural environments in which organic materials and microorganisms are, or have been present (Visser, 1973). Humic acids have been used in medicines at a dosage of between 0.9 and 1.8 g daily for the treatment of hyperacidity and other gastric disturbances in humans (Gramsch, 1961; Reichert, 1966). No unfavourable side effects have been observed at the above-mentioned doses.

Humic acids have also been successfully used as anti-inflammatory agents because of their local anti-inflammatory, hyperaemic and analgesic properties (Salz, 1974; Motohisa et al., 1974) and as a systemic treatment for anaemia and hypercholesterolaemia (Soloveyva and Lotosh. 1984).

Peat extracts have been used in therapeutic baths for the treatment of various conditions for many years (Brandt, 1964; Eichelsdörfer, 1976). The antiseptic properties of peat were first recognised during World War 1 when it was applied directly on to battle wounds to prevent infection (Haanel, 1924). The possible application of coal-derived humic acid and fulvic acid as antimicrobials, has recently been investigated by Cloete et al. (1990) of the Department of Microbiology, University of Pretoria.

More recently, humate has been used in the treatment of Von Willebrand disease (Lopez-Fernandez et al., 1992). Patients were treated with an infusion of 35 mg/kg body weight after which normal VIII levels were achieved.

It has been reported that humic acids derived from either the decomposition of organic matter (Sato et al., 1986) or the oxidation of coal (Bernacchi et al., 1996) do not act as mutagens, but interestingly, may rather on the other hand behave as desmutagens (Takahiko et al., 1986) by inhibiting the mutagenicities of selected mutagens.

The anti-tumour properties of humic acids were first investigated in vivo by Zsindely et al. (1971) who reported that mice which received 10–40 mg humic acids orally for 5 days after experimental induction of cancer by administration of ascites sarcoma or lymphoma (IP) showed a greatly reduced tumour load 10 days later. They also found that the humic acid treatment resulted in a 20–25% decrease in the RNA and DNA content of tumour cells. Humic acids have also been shown to control uterine cancer in rats (Davies, 1996).

Since they are highly surface-active (Visser, 1982), these acids may act on the membranes of malignant cells, which often differ in structure and function of normal cells (Bennet & Connon, 1957). Adamek (1976) reported that a peat preparation administered orally, rectally or intramuscularly at tumour sites resulted in their arrest or regression.

Antiviral properties, at a concentration of 100 µg/ml of ammonium humate in vitro have been described by Thiel et al. (1981) resulting in the successful use of this agent as a topical treatment for herpes virus-induced skin diseases (Kl öcking et al., 1983). Schneider et al. (1996) reported on the anti-HIV activity of synthetic humate analogues derived from hydroquinone. These compounds inhibited HIV-1 infection of MT-2 cells with an impressively low $IC_{50}$ of 50–300 ng/ml. The infectivity of HIV particles was inhibited by interference with the CD4-induced proteolytic cleavage of the V3-loop of virion gp120SU.

SUMMARY OF THE INVENTION

According to a first aspect of the invention, there is provided a humic acid, salt, ester or derivative thereof, for use in the manufacture of a medicament for use in stimulating lymphocytes in a subject.

According to a preferred form of the invention, there is provided the use of a humic acid, salt, ester or derivative thereof, in the manufacture of a medicament for use in stimulating the $T_H1$ and $T_H2$ lymphocytes in a subject. Stimulation of the $T_H1$ and $T_H2$ lymphocytes in a subject allows the medicament to be used, for example, in the treatment of viral and bacterial infections, and more particularly HIV infections, cancer and opportunistic diseases.

The invention provides, according to a particularly preferred aspect, a medicament of the type described above for oral administration. It has been found that the humic acid, salt, ester or derivative thereof is rapidly taken up by the subject if administered orally.

The invention further provides a method of stimulating lymphocytes in a subject which includes the steps of administering a humic acid, salt, ester or derivative thereof, to the subject. The amount of humic acid, salt, ester or derivative thereof, administered to the subject will be effective to stimulate lymphocytes in the subject.

The subject may be a human, animal or bird.

Examples of specific uses of the humic acid, salt, ester or derivative thereof are inhibiting, viral and bacterial infections, inhibiting cancer growth, the treatment of myalgic encephalitis (ME) associated with viral infections and a depressed immune system, inflammation, pain and fever.

The active ingredient in the practice of the invention is humic acid, a salt, ester or derivative thereof. Humic acid is a complex mixture of macromolecular organic substances which are not soluble in water under acidic conditions, i.e. at pH below 2, but are soluble at higher pH values.

The invention has particular application to a humic acid which may be produced, for example, by the wet oxidation process described in U.S Pat. No. 4,912,256. Such humic acid is hereinafter referred to as "oxihumic acid". The potassium or sodium salt of a humic acid, particularly oxihumic acid, may be produced by the method described in U.S. Pat. No. 5,004,831. Oxihumic acid also has no defined structure. It is a complex mixture of organic compounds. It is acidic in nature, due to its carboxylic and phenolic groups. Oxihumic acid is practically insoluble at low pH in water, but becomes soluble in alkaline aqueous medium.

Oxihumic acid can, therefore, be regarded as a relatively high molecular mass product containing carboxylic and phenolic groups. Oxihumic acid compared to so-called natural humic acids has a relatively high degree of aromaticity. A typical functional group analysis of oxihumic acid is given below:

| Total acid groups: | 3–13 meq/g, preferably | 5.4 meq/g |
| Carboxylic groups: | 0.5–12 meq/g, preferably | 2.2 meq/g |
| Phenolic groups: | 0.5–9 meq/g, preferably | 3.2 meq/g |

The humic acid, salt, ester or derivative thereof will preferably be provided in a pharmaceutical composition form suitable for oral administration. A particularly suitable form is a capsule. The active ingredient may be present in the capsule with or without excipients.

The invention provides according to yet another aspect, a pharmaceutical composition comprising oxihumic acid, salt, ester or derivative thereof, as an active ingredient. The composition has particular application in the treatment and the control of viral infections such as HIV infections, and cancer. For these applications, the composition is preferably administered orally.

DESCRIPTION OF EMBODIMENTS

Potassium oxihumate, having the preferred functional group analysis mentioned above and hereinafter referred to as "oxihumate", has been subjected to a number of in vitro and in vivo studies and these are described hereinafter.

i) Effects of Oxihumate on the Proliferative Responses of Phytohaemagglutinin (PHA)-stimulated Human Lymphocytes In these experiments suspensions of purified human monocyte depleted lymphocytes, at a concentration of $1 \times 10^6$ lymphocytes/ml in RPMI medium supplemented with 10% fetal calf serum (FCS), were added to the wells of microtitre plates. To some of the wells a mitogen (phytohaemagglutinin, PHA) was added at a concentration of 2.5 µg/ml. The cultures were incubated either with or without oxihumate (5–100 µg/ml) for 72 h at 37° C. in an atmosphere of 5% $CO_2$. The extent of lymphocyte proliferation was assayed by MTT [3-(4.5-dimethylthiazol-2-yl)-2.5-diphenyl tetrazolium bromide] reactivity which detects only viable cells.

Figure 1:
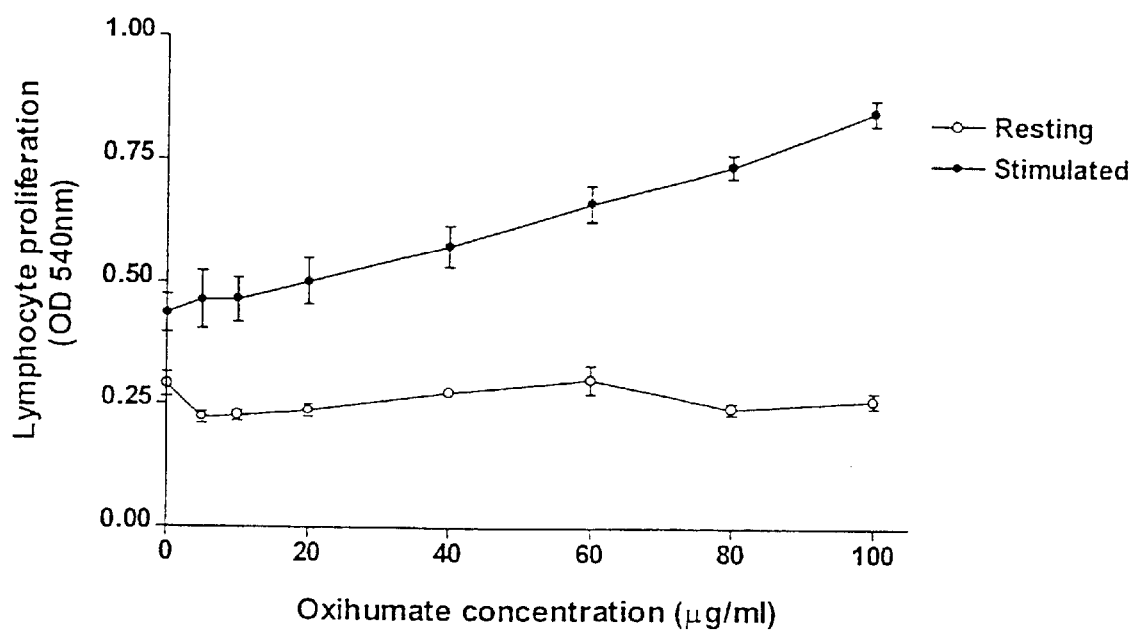
FIG. 1 is a graph illustrating the effects of oxihumate on resting and PHA-stimulated, monocyte depleted, human lymphocyte cultures.

Oxihumate had no effect on resting lymphocytes but increased the proliferative response of PHA-stimulated lymphocytes in a dose-related manner (FIG. 1).

Figure 2:
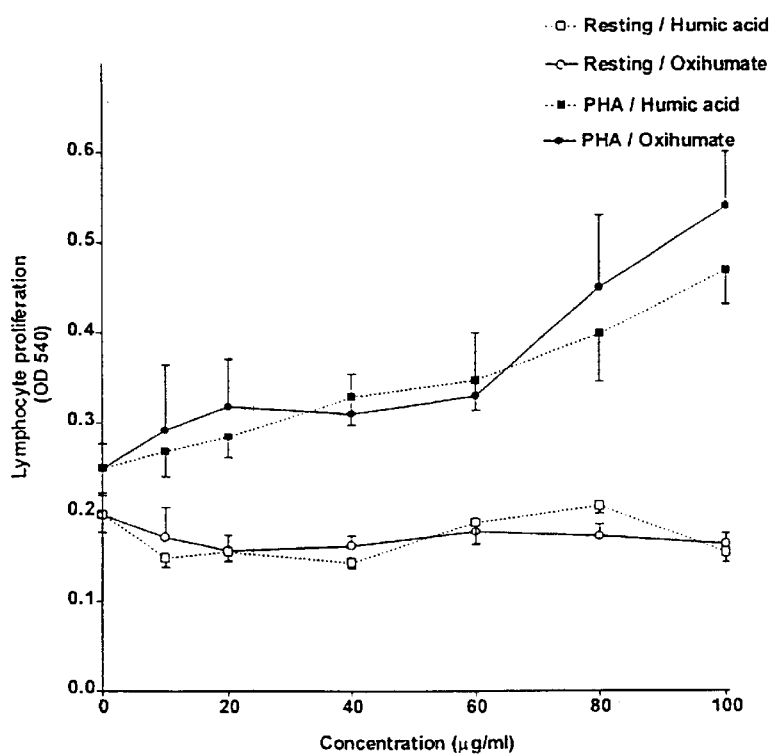
FIG. 2 is a graph providing comparative results of synthetic humic acid and oxihumate on resting and PHA-stimulated, monocyte-depleted human lymphocyte cultures.
Figure 3:
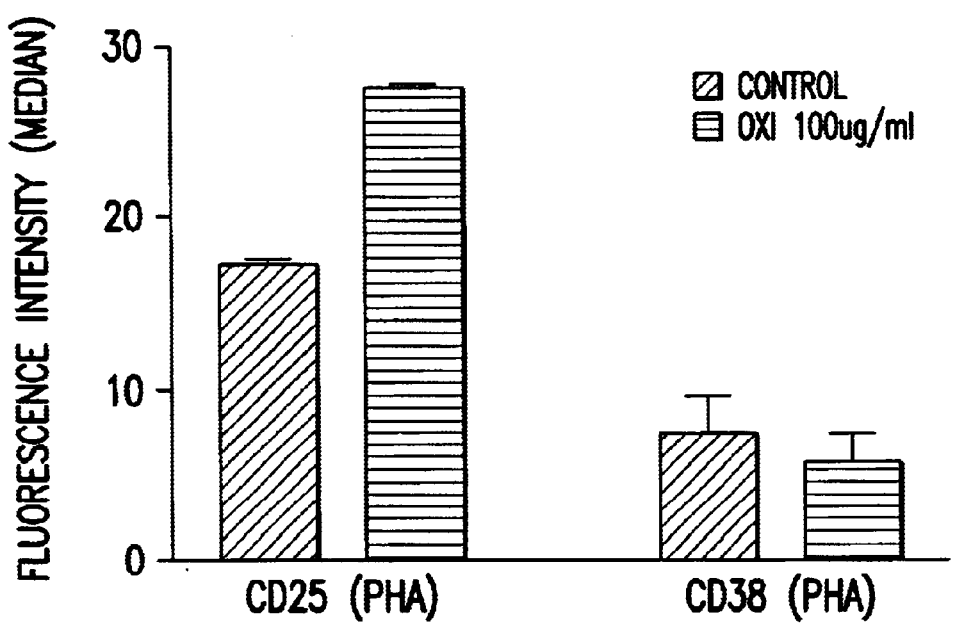
FIG. 3 is a graph showing the effect on the expression of the activity markers CD25 (T-cell receptor) and CD38 on PHA-stimulated human lymphocytes.
Figure 4:
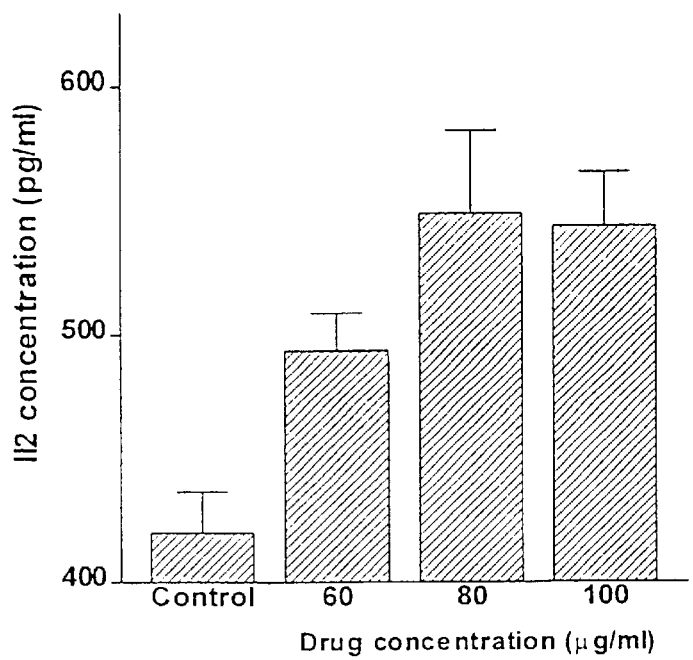
FIG. 4 is a graph showing the effect of oxihumate on interleukin-2 production by stimulated human lymphocytes.
Figure 5:
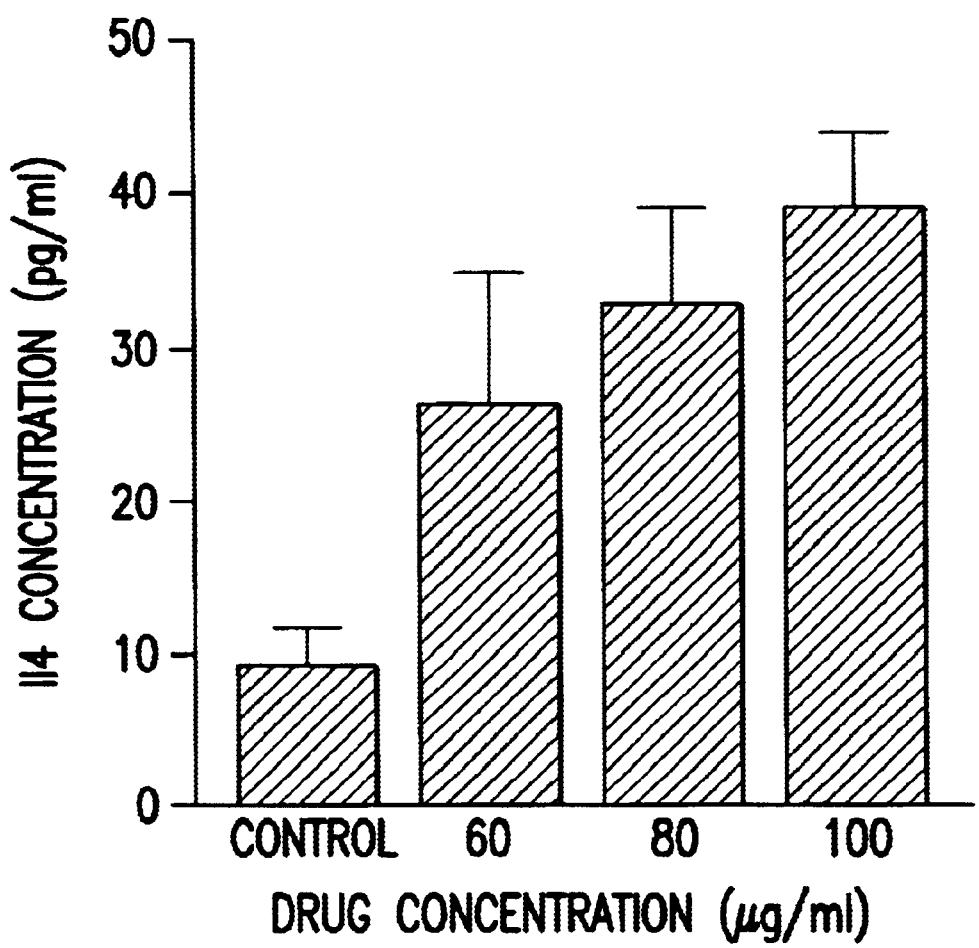
FIG. 5 is a graph showing the effect of oxihumate on interleukin-4 production by PHA-stimulated human lymphocytes.
Figure 6:
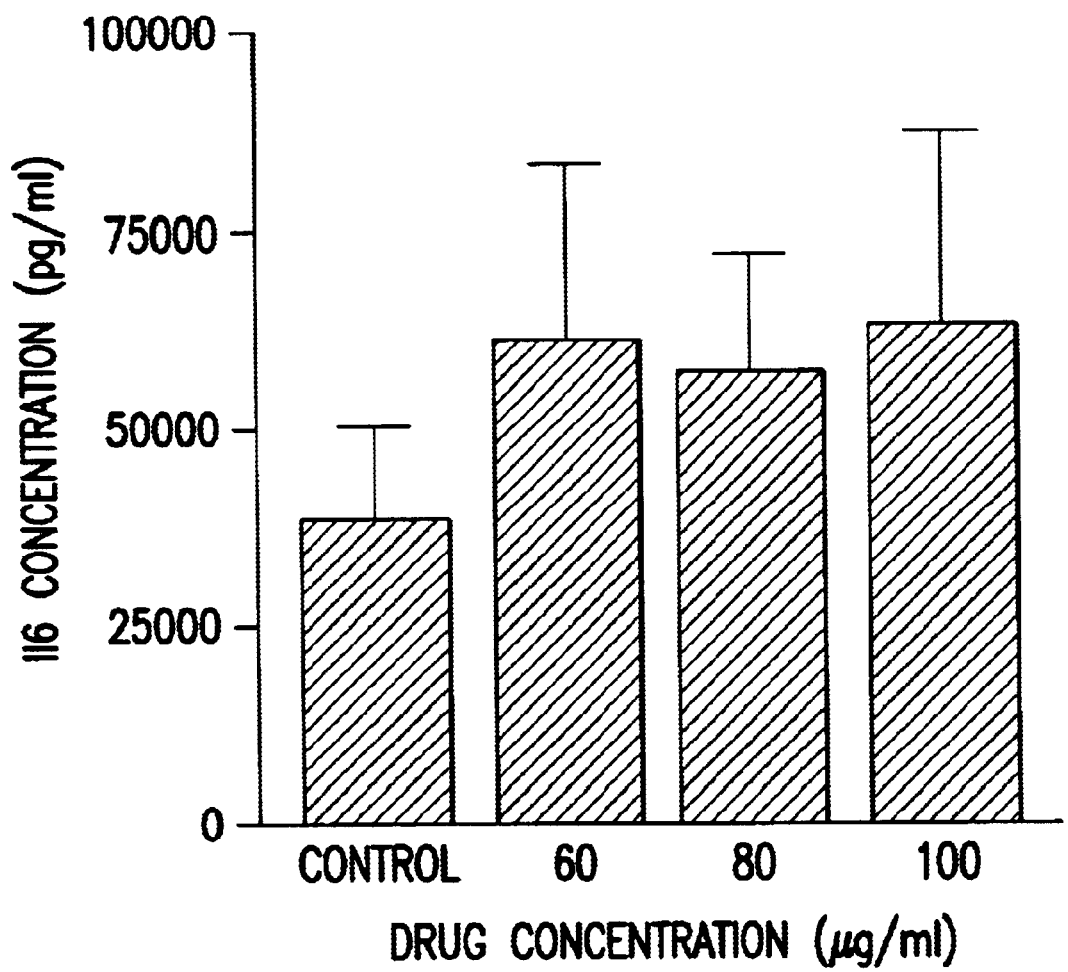
FIG. 6 is a graph showing the effect of oxihumate on interleukin-6 production by stimulated human lymphocytes.

Similar results were obtained with a synthetic humic acid (Sigma Chemicals Co., St. Louis, Mo.). Oxihumate was on average more effective at 80 and 100 μg/ml than the synthetic humic acid (FIG. 2).

ii) Effects of Oxihumate on the Expression of the Activation Markers CD25 and CD38 on Human Lymphocytes Resting or PHA-stimulated human lymphocytes were incubated in test tubes at a concentration of $1 \times 10^6$ cells/ml in RPMI medium supplemented with 10% FCS for 72 h in either the presence or absence of oxihumate (100 μg/ml) and the expression of the IL-2-receptor (CD25) and CD38 (a molecule involved in signal transduction and cellular adhesion), was analysed using a flow cytometer (Coulter Epics XL-MCL). It was observed that oxihumate had no effect on the expression of either CD25 or CD38 on resting lymphocytes (results not shown), but increased the expression of CD25 significantly on PHA-stimulated cells, whereas the expression of CD38 on these cells decreased with oxihumate treatment (FIG. 3).

iii) Interleukin 2 (IL-2), Interleukin 4 (IL-4) and Interleukin 6 (IL-6) Production by Human Lymphocytes PHA-stimulated human lymphocyte cultures were treated as above with oxihumate at 60, 80 and 100 μg/ml for 48 h, whereafter the cells were centrifuged and the cell-free supernatants assayed for IL-2. IL-4 or IL-6 levels, using a Biotrak TM human ELISA system from Amersham TM (Amersham International Plc, Buckinghamshire, England). Results obtained from 4 different experiments are shown in FIGS. 4 to 6. Oxihumate caused a statistically significant increase in IL-2 and IL-4 production by stimulated lymphocytes at all three concentrations tested (FIGS. 4 and 5). A slight but not significant increase in IL-6 production by oxihumate was also observed (FIG. 6).

iv) Increased Antibody Production Against Newcastle Disease in Chickens Treated with Oxihumate In an experiment to determine the efficacy of oxihumate to control *Mycoplasma gallisepticum* infection in Ross 308 broiler chickens, 2550 day-old chickens were divided into 5 groups, infected with the organism and treated as follows:

Treatment 1: control, untreated

Treatments 2–4: 50, 100 or 200 mg oxihumate/kg/day

Treatment 5: Baytril, 10 mg/kg/day for 3 days in the first week of life, followed by a one day treatment at 21 days of age All chickens were vaccinated at 16 days of age for Newcastle disease and Gumboro to establish the effect oxihumate has on the production of antibodies against these diseases in chickens.

Blood samples of 15 birds per treatment were taken at 28 days and 45 birds per treatment at 42 days to determine antibody titers against Newcastle and Gumboro diseases using the ELISA test system. No difference in antibody titers against Gumboro between the treatment and control groups was found (results not shown).

Figure 7:
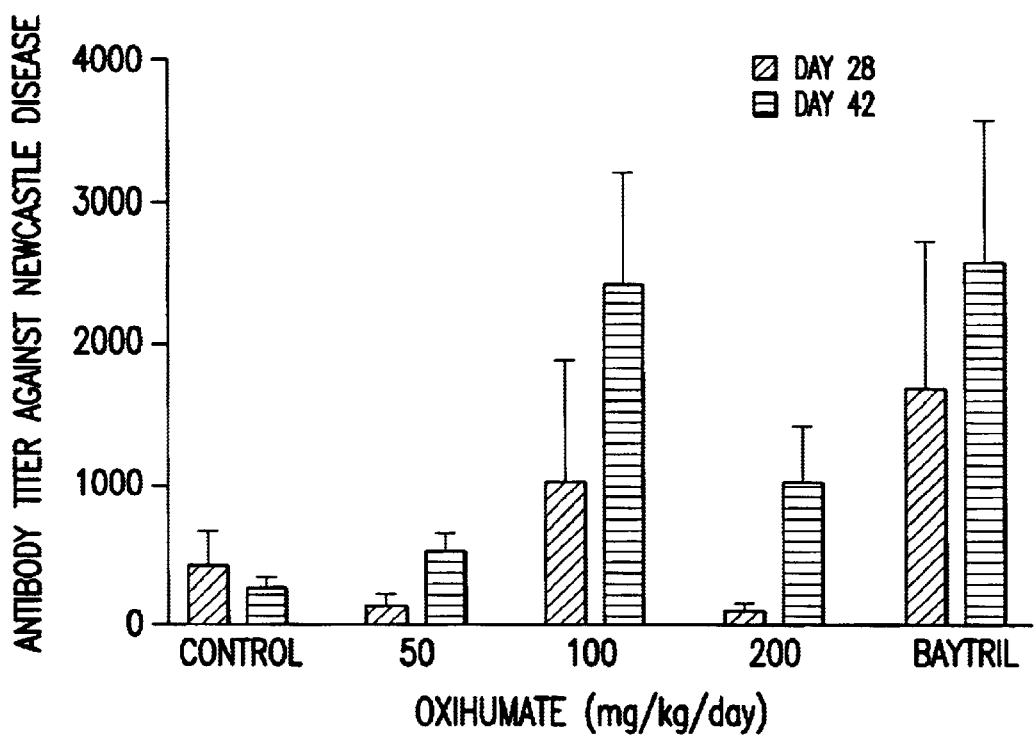
FIG. 7 is a graph showing the effect of a 28- and 42-day treatment of oxihumate (50, 100 and 200 mg/kg/day) and baytril on antibody production against Newcastle disease after vaccination.

However both the Baytril treatment group and the group treated with 100 mg oxihumate/kg/day showed a two to four fold increase in titers against Newcastle disease at day 28 and 42 (FIG. 7) indicating the ability of these two compounds to stimulate the humoral immune response.

Results on the presence of *M. gallisepticum* in the treated and control groups are not yet available.

An increase in IL-2. necessary for cell-mediated ($T_H1$-type) immunity, as well as an increase in IL-4 and IL-6, necessary for humoral ($T_H2$-type) immunity, indicate that this compound can be an effective immunostimulant which may prove suitable for application by patients suffering from viral and bacterial infections.

v) Interleukin 10 (IL-10) Production by Oxihumate Treated Lymphocytes

PHA-stimulated human lymphocyte cultures were treated with oxihumate at 60, 80 and 100 μg/ml for 48 h, whereafter the cells were centrifuged and the cell-free supernatants assayed for IL-10 levels, using Biotrak high sensitivity IL-10 ELISA system from Amersham TM (Amersham International Plc, Buckinghamshire, England).

Figure 8:
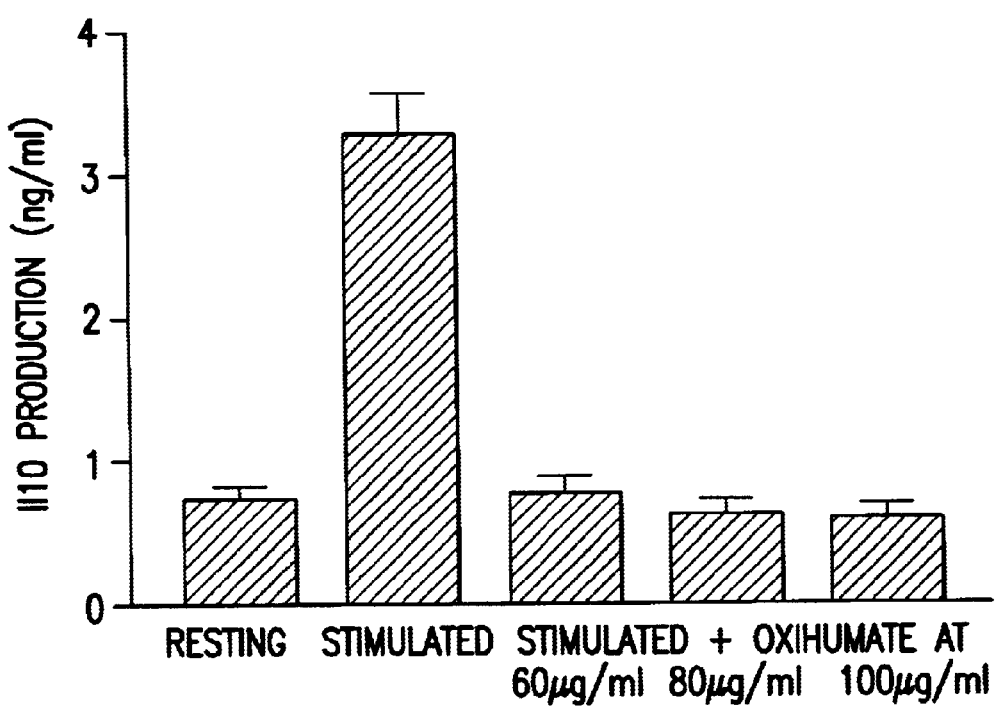
FIG. 8 is a graph showing the effect of oxihumate on interleukin-10 production by stimulated human lymphocytes.

The results obtained from 3 different experiments are shown in FIG. 8. Oxihumate inhibited IL-10 production by PHA-stimulated lymphocytes at all three concentrations tested.

These results confirm the IL-2 results indicating an increase in $T_H1$ cell activity.

vi) Leukotriene B4 (LTB4) Production by Oxihumate Treated Lymphocytes

Phorbol 12-myristate 13-acetate (PMA at 100 ng/ml)-stimulated human lymphocyte cultures ($1 \times 10^6$ lmphocytes/ml in RPMI medium supplemented with 10% FCS) were treated with oxihumate at 60, 80 and 100 μg/ml for 20 min at 37° C. The cultures were centrifuged and the supernatants assayed for LTB4 levels, using Biotrak LTB4 enzyme immuno-assay system from Amersham International Plc, Buckinghamshire, England.

Figure 9A:
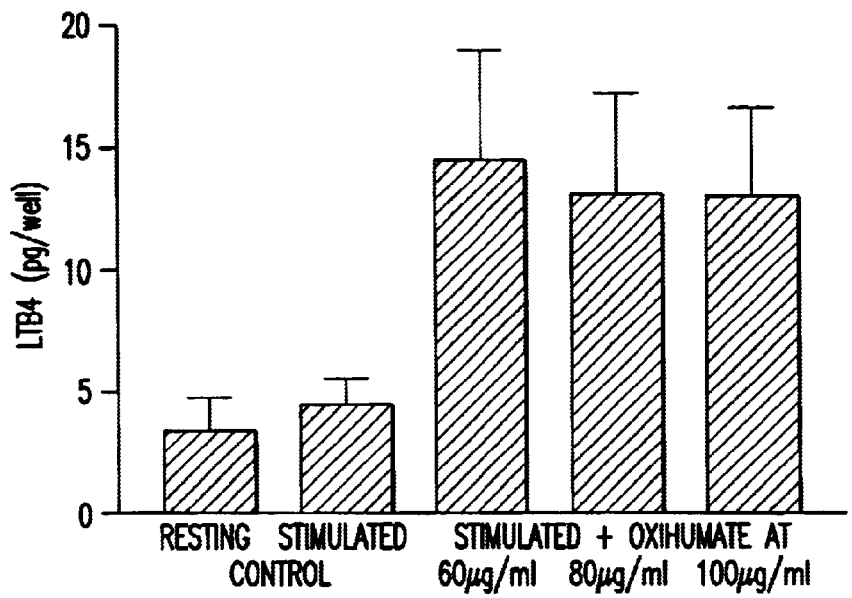
FIG. 9 comprises two graphs illustrating the effects of a 20-minute treatment of oxihumate on leukotriene B4 production by PMA-stimulated human lymphocytes.
Figure 9B:
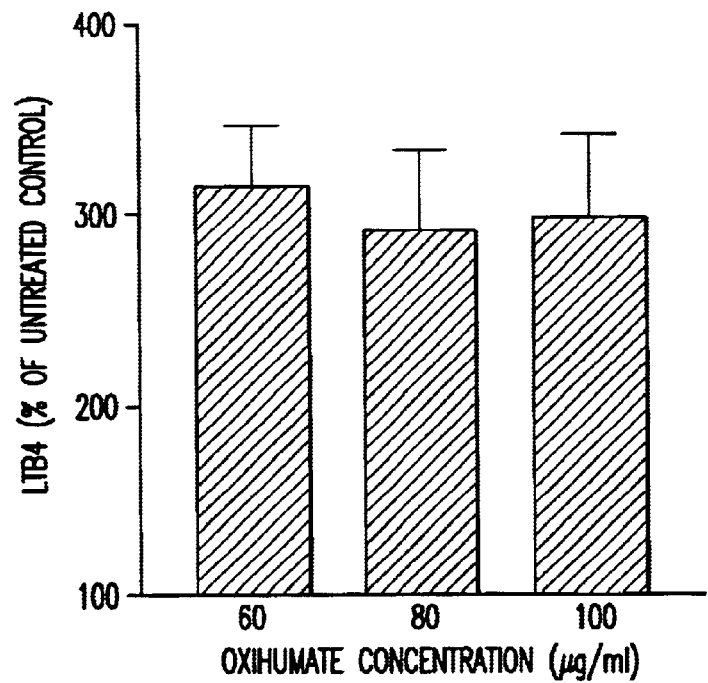

The results obtained from 4 different experiments are shown in FIG. 9. Oxihumate increased LTB4 production by PMA-stimulated human lymphocytes more than 300% compared to the untreated controls at all 3 concentrations tested (FIG. 9B).

The role of leukotrienes in the immune response is less clear. Various researchers have reported that LTB4 can act as a multifunctional regulator of cytokine production and that it is able to stimulate both $T_H1$ and $T_H2$ subpopulations. LTB4 not only plays an important role in the induction of the production of IL-2 but also enhances the activity of cytotoxic T-cells and this could possibly explain the increase in IL-2 production as well as the increase in cytotoxicity of oxihumate-treated lymphocyte cultures.

vii) Prostaglandin E2 (PGE2) Production by Oxihumate Treated Lymphocytes

Phorbol 12-myristate 13-acetate (PMA. at 100 ng/ml)-stimulated human lymphocyte cultures ($1 \times 10^6$ lymphocytes/ml in RPMI medium supplemented with 10% FCS) were treated with oxihumate at 60, 80 and 100 μg/ml for 20 min at 37° C. The cultures were centrifuged and the supernatants assayed for PGE2 levels, using Biotrak PGE2 enzyme immuno-assay system from Amersham International Plc, Buckinghamshire, England.

Figure 10A:
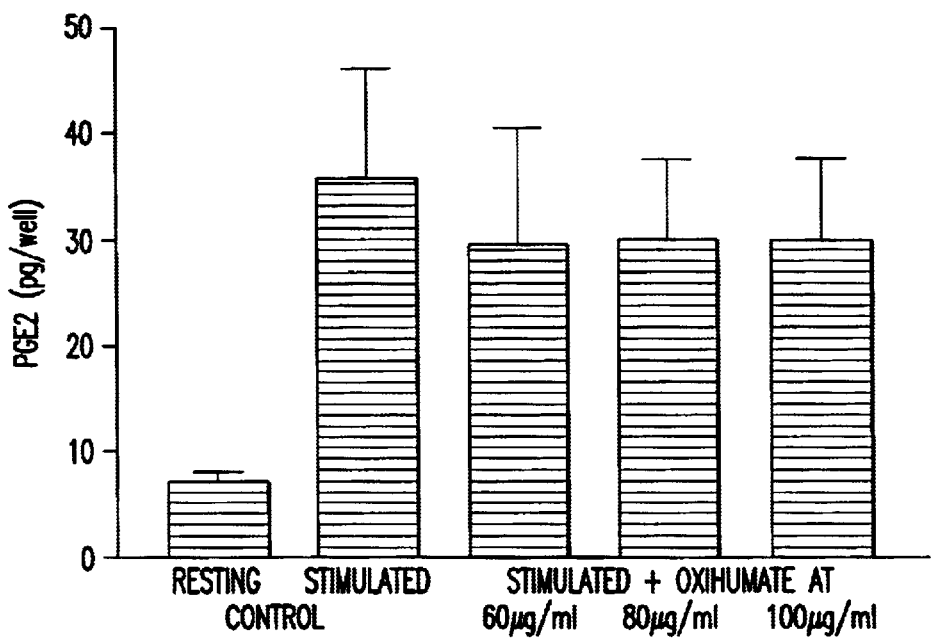
FIG. 10 comprises two graphs illustrating the effects of a 20-minute treatment of oxihumate on prostaglandin E2 production by PMA-stimulated human lymphocytes.
Figure 10B:
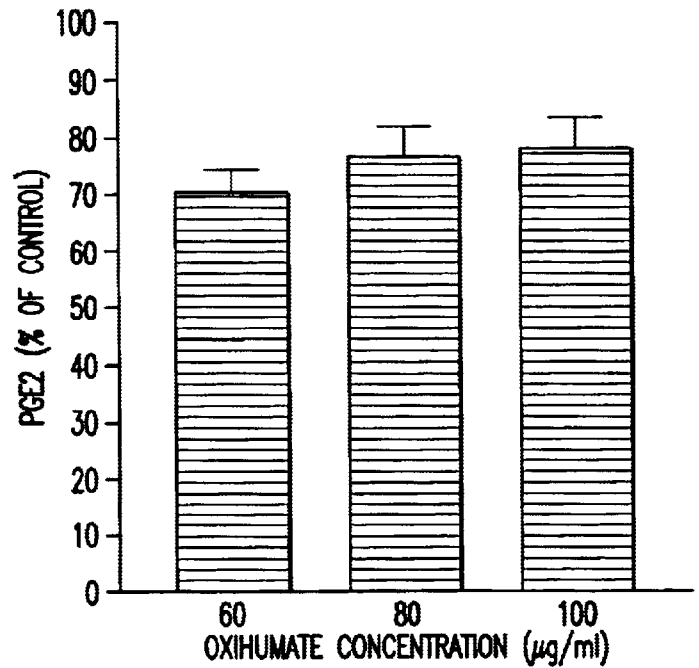

The results obtained from 8 different experiments are shown in FIG. 10. Oxihumate decreased PGE2 production by PMA-stimulated human lymphocytes by between 20 and 30% compared with the untreated controls at all 3 concentrations tested (FIG. 10B).

PGE2 is recognized for its capacity to induce pain and fever. It inhibits T cell proliferation by down-regulating $T_H1$-associated cytokine (IFN-λ, TNF-β and IL-2) production. Although oxihumate (up to 100 μg/ml) mediated inhibition of PGE2 production did not exceed 30% of control values, a decreased level may contribute to an increase in lymphocyte proliferation and $T_H1$-associated cytokines.

viii) Tumor Necrosis Factor (TNF) Production by Oxihumate Treated Lymphocytes

PHA stimulated human lymphocytes were treated with oxihumate at 10, 20, 40, 60, 80 and 100 μg/ml for 24 h at 37°

C. and the supernatants assayed for TNF levels, using Biotrak TNF-α enzyme immuno-assay system from Amersham International Plc, Buckinghamshire, England.

Figure 11:
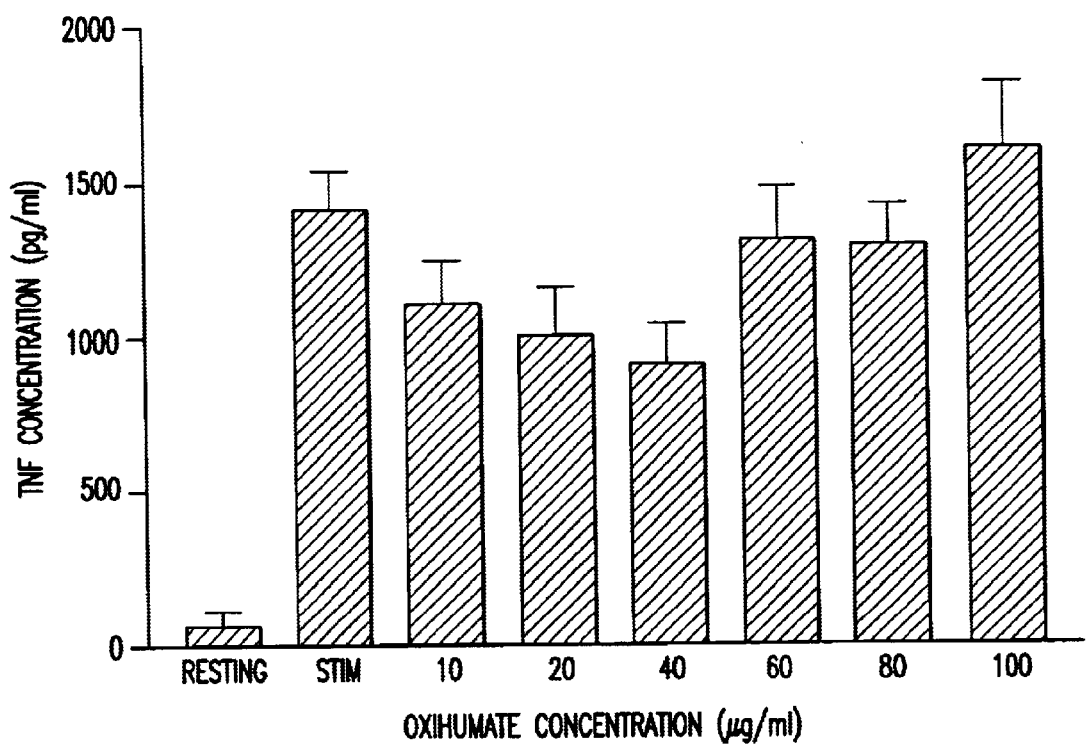
FIG. 11 is a graph showing the effects of oxihumate on the production of tumor necrosis factor by PHA-stimulated human lymphocytes.

Oxihumate decreased the production of TNF by PHA-stimulated human lymphocytes significantly at concentrations of 10, 20 and 40 µg/ml compared to the untreated control (FIG. 11).

TNF plays an important role in inflammation and acts on endothelium, leukocytes and fibroblasts especially in the induction of the systemic acute-phase reactions associated with infection or injury. It induces the synthesis of endothelial adhesion molecules, other cytokines, growth factors and nitric oxides. TNF also causes aggregation and the priming of neutrophils leading to augmented responses of these cells to other mediators and the release of proteolytic enzymes from mesenchemal cells, thus contributing to tissue damage. A decreased production of TNF would therefore lead to a favourable reaction during both acute as well as chronic inflammatory conditions.

ix) Expression of CR3 by Oxihumate Treated Polymorphonuclear Leukocytes

Human leukocytes were treated with oxihumate (10–100 ug/ml) for 30 min in RPMI supplemented with 10% fetal calf serum in the presence or absence of phorbol myristate acetate (PMA), and assayed for the expression of CR3 on the cell membranes of polymorphonuclear leukocytes (PMNL) using a flow cytometer (Coulter Epics XL-MCL).

Figure 12:
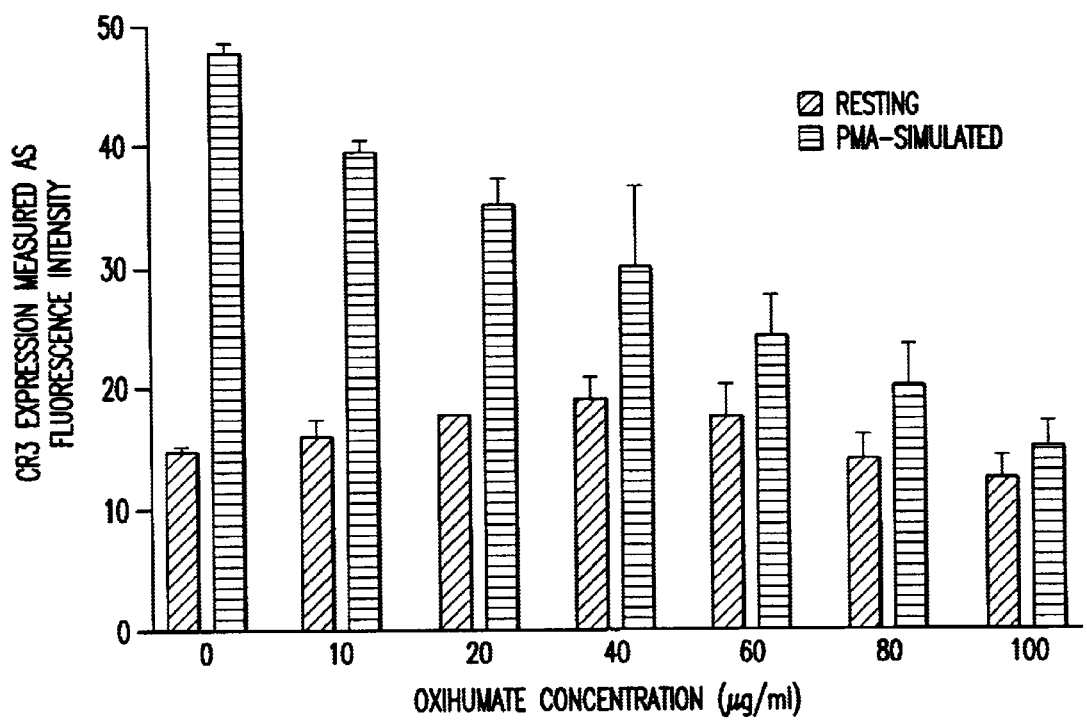
FIG. 12 is a graph showing the effect of a 30-minute oxihumate treatment on CR3 expression by resting and PMA-stimulated human neutrophils.

Oxihumate decreases the expression of CR3 on PMA-stimulated, but not resting, PMNL significantly in a dose related fashion at all 6 concentrations tested (FIG. 12). This property is shared by various new and effective anti-inflammatory drugs such as theophylline and ibudilast. More over anti-CR3 monoconal antibodies have been used successfully in the treatment of induced inflammation disorders in experimental animals.

CR3 is a member of a family of leukocyte proteins that mediates adhesion in a variety of cell to cell and cell to substrate interactions. It plays a crucial role in phagocytosis, diapedesis and the movement of leukocytes through an endothelial monolayer into tissues. Adhesion molecules therefore play a key role in inflammatory processes present in diseases such as autoimmune diseases as well as allergic reactions. Inhibition of the expression of adhesion molecules such as CR3 by oxihumate should make it an effective drug in the treatment of inflammatory diseases.

x) Cytotoxic Activity of Oxihumate-treated Human Lymphocytes

PLC cells (a human liver cancer cell line), ($5 \times 10^5$/ml) were cultured in RPMI medium supplemented with 10% fetal calf serum (FCS) for 72 h in 96 well round-bottom microtitre plates, either in the presence or absence of human lymphocytes (1:2 ratio for target cells:lymphocytes). These cultures were treated with oxihumate (5–100 µg/ml) for 72 h, after which the lymphocytes were removed by washing and the mitochondrial activity of the adherent PLC cells determined using a standard MTT assay.

Figure 13:
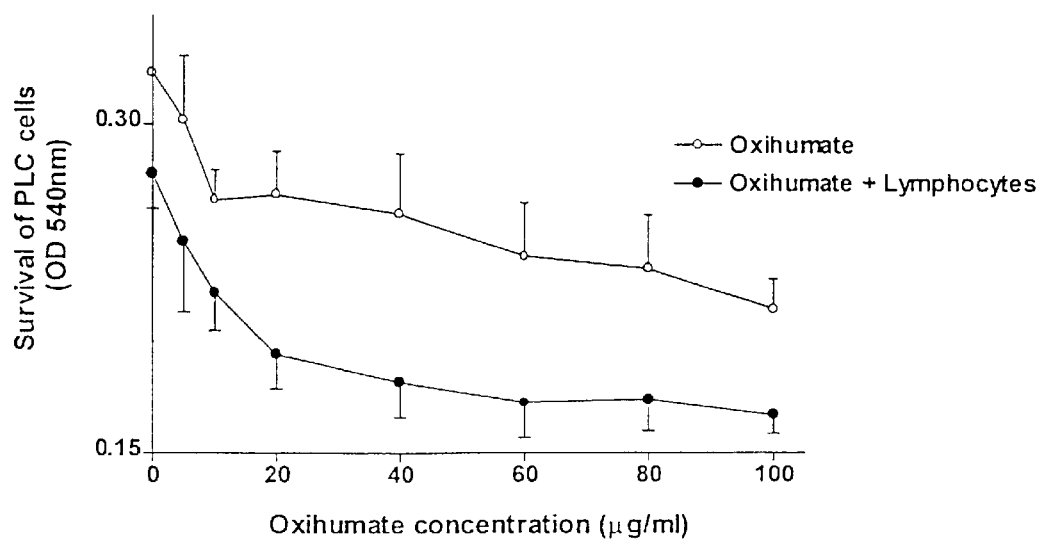
FIG. 13 is a graph showing the effect of oxihumate and oxihumate-treated human lymphocytes on the survival of a human liver cancer cell line (PLC)

Oxihumate inhibited the growth of PLC cells at concentrations of 10 µg/ml and higher (FIG. 13). The addition of human lymphocytes to the system significantly increased the level of inhibition (FIG. 13).

xi) Antiviral Activity of Oxihumate Against Herpes Simplex Virus Type 1 (HSV-1) and Coxsackie Virus Type 1 (CBV-1) in vitro To investigate the effect of oxihumate on the replication of each virus, 42 h old monolayers of vervet monkey kidney (VK) cells were infected with either HSV-1 or CBV-1. After one hour the unbound virus was removed and the cells treated with various concentrations of oxihumate in serum-free MEM (minimum Eagles' medium) at 37° C. in a humidified $CO_2$ atmosphere for 7 days.

To investigate the effect of oxihumate on viral absorption to cells oxihumate and the virus suspension were added simultaneously to the cell cultures and incubated at 37° C. in a humidified $CO_2$ atmosphere for 7 days.

To investigate the effect of oxihumate on the infectivity of viral particles, equal volumes of viral suspensions were mixed with dilutions of oxihumate and incubated for one hour at 37° C. The oxihumate/virus suspension was added to a 24 h culture and incubated at 37° C. in a humidified $CO_2$ atmosphere for 7 days. The appearance of a cytopathic effect (CPE) was considered to be indicative of a lack of inhibition of viral replication. The percentage CPE reported is the mean of the percentage CPE noted in each of the 6 experimental wells.

In all three methods cells were examined by light microscopy daily for 7 days.

Figure 14:
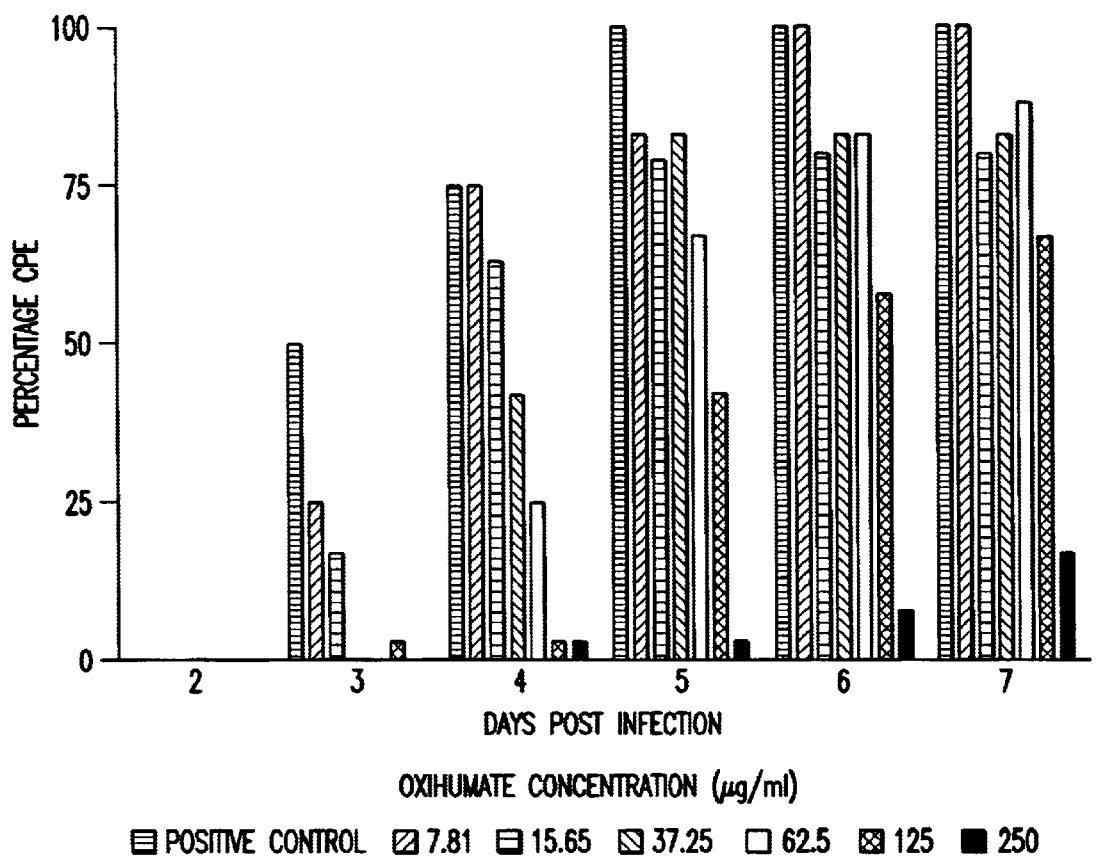
FIG. 14 is a graph showing the effect of oxihumate on HSV-1 replication after prior adsorption of the virus to the cell cultures.
Figure 15:
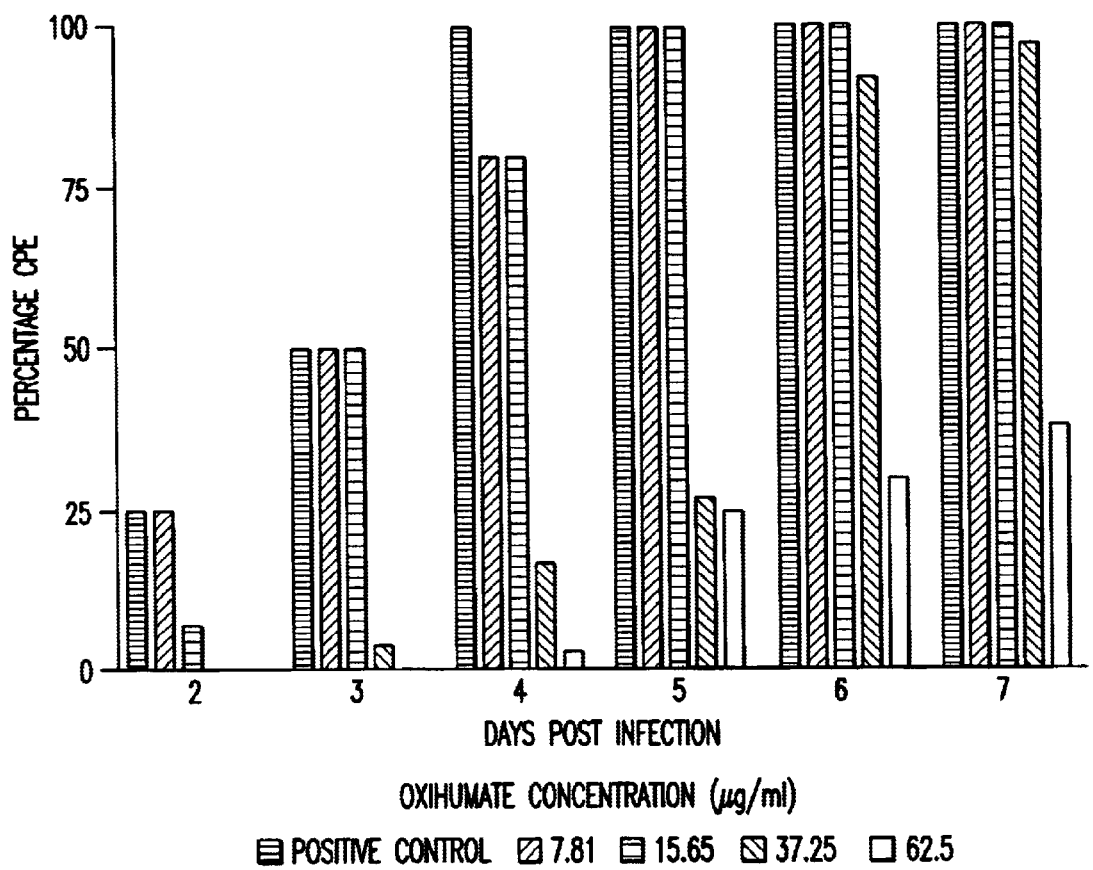
FIG. 15 is a graph showing the effect of oxihumate on HSV-1 replications when added simultaneously to the cell cultures.

Oxihumate (3.9–1000 µg/ml) had no effect on the adsorption and/or replication of CBV-1 (results not shown). In contrast to this, marked anti-viral activity against HSV-1 was noted at concentrations of 62.5 to 250 µg/ml (FIGS. 14 and 15). Because the virus was more sensitive when added simultaneously with the compounds to the cells (FIG. 15), the data therefore suggests that oxihumate interferes with the adsorption to and subsequent replication of HSV-1 in cell culture.

When the infectivity on both CBV-1 and HSV-1 were assessed after exposure to the different concentrations of oxihumate for one hour at 37° C. a total inhibition of infectivity of HSV-1 as well as CBV-1 was noted at concentrations of 62.5–500 µg/ml and 125–500 µg/ml respectively. (Table 1).

TABLE 1

Dose response of Coxsackie B virus type 1 on vervet monkey kidney cells after exposure to oxihumate at 37° C. for 1 hour
PERCENTAGE CYTOPATHIC EFFECT[a] POST-INFECTION

| Oxihumate Concentration (µg/ml) | 24 h | 48 h | 72 h | 96 h | 120 h | 144 h | 168 h |
|---|---|---|---|---|---|---|---|
| Negative control | 0 | 0 | 0 | 0 | 0 | 0 | 0 |
| Positive control | 0 | 19 | 100 | 100 | 100 | 100 | 100 |
| 3.9 | 0 | 13 | 25 | 75 | 100 | 100 | 100 |
| 7.81 | 0 | 6 | 25 | 50 | 50 | 50 | 50 |
| 15.65 | 0 | 6 | 25 | 38 | 50 | 50 | 50 |
| 31.25 | 0 | 6 | 25 | 25 | 25 | 25 | 25 |
| 62.5 | 0 | 0 | 0 | 0 | 0 | 0 | 25 |
| 125 | 0 | 0 | 0 | 0 | 0 | 0 | 0 |
| 250 | 0 | 0 | 0 | 0 | 0 | 0 | 0 |
| 500 | 0 | 0 | 0 | 0 | 0 | 0 | 0 |

[a]The percentage CPE reported is the mean of the percentage CPB noted in each of the 4 experimental wells.

xii) Antiviral Activity of Oxihumate Against HIV-1 in vitro

Figure 16:
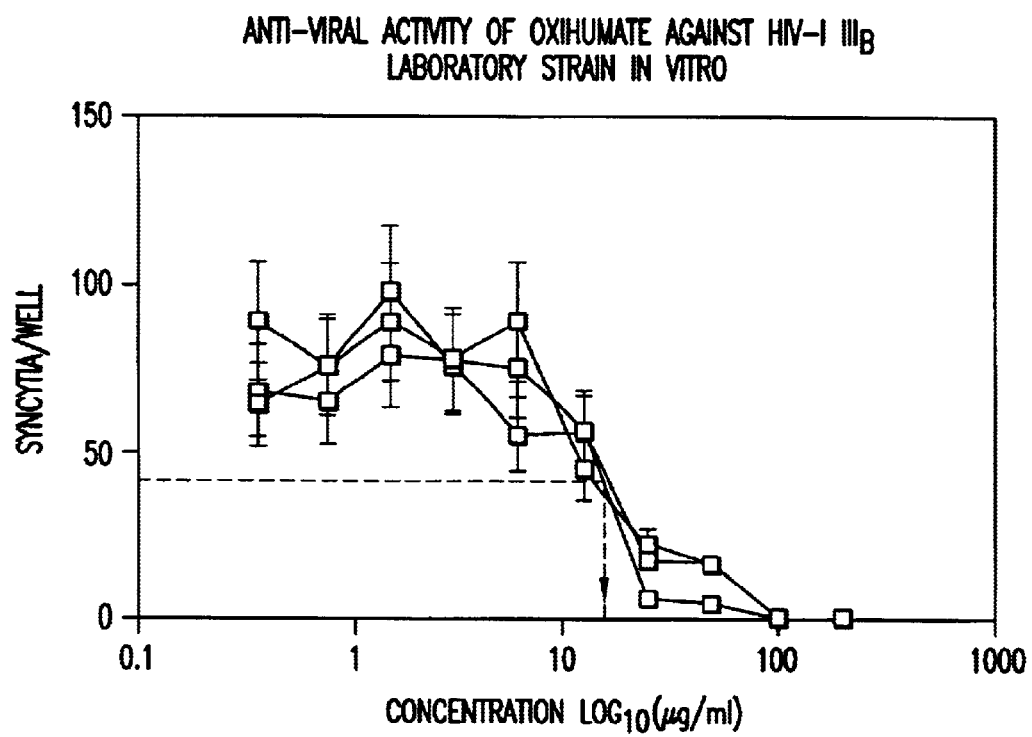
FIG. 16 is a graph showing the anti-viral activity of oxihumate against an HIV-1 III$_B$ laboratory stain in vitro.

To investigate the effect of oxihumate on the replication of HIV-1 III$_B$ laboratory strain, a suspension of the virus (HIV-1) was added to oxihumate concentrations between 0.35 and 200 µg/ml for 15 min at room temperature prior to the addition of MT-2 cells (a CD4 positive human lymphocyte cell line). The cell cultures were incubated at 37° C. in a humidified $CO_2$ atmosphere for 5 days after which syncytia formation was determined by light microscopy. The results of three experiments done in triplicate can be seen in FIG. 16. A 50% inhibition of viral growth was observed at an oxihumate concentration of 16 µg/ml.

Figure 17:
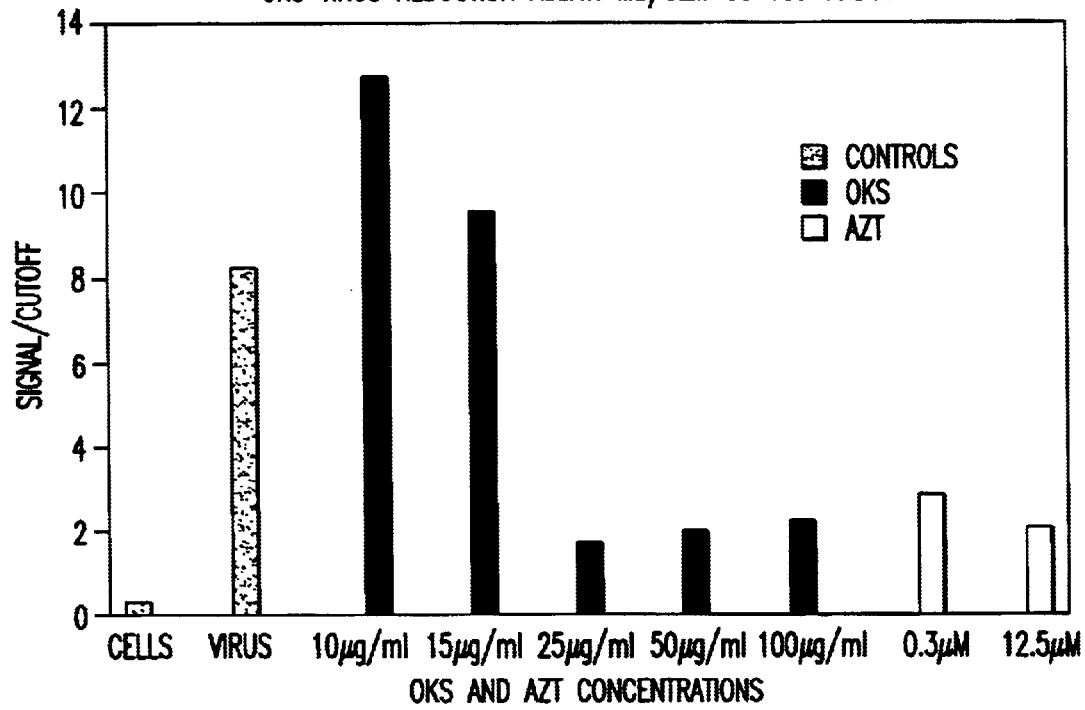
FIG. 17 is a graph showing the anti-viral activity of oxihumate against an HIV-1 III$_B$ laboratory stain in vitro.
Figure 18:
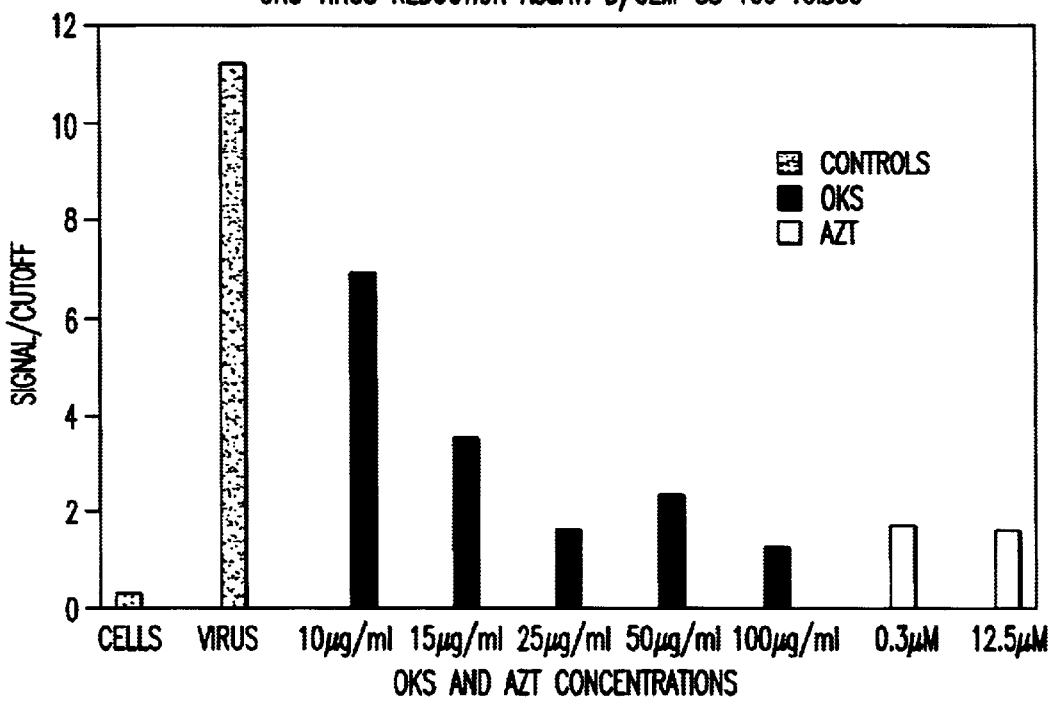
FIG. 18 is a graph showing the anti-viral activity of oxihumate against an HIV-1D isolate in vitro.

These results were confirmed by a different research group using the same (HIV-1 III$_B$ laboratory strain) and a different (HIV-1 D) isolate of HIV-1 (FIGS. 17 and 18). In these cases the activity of oxihumate was compared to that of AZT. Oxihumate at 25 μg/ml reduced viral growth in both cases to the same level as 0.3 μM and 12.5 μM AZT.

Although inhibition of HIV-1 in cell cultures by a synthetic humate analogue has been described by Schneider et al 1996, these results are the first to document the anti-HIV-1 activity of oxihumate.

(xiii) Phase I Clinical Trial of Oral Oxihumate in HIV-infected Patients

HIV-infected patients have been treated with either 2 g, 4 g or 6 g oxihumate per day for two weeks.

Nine patients were randomized in a double-blind fashion in each group into 2 arms: one arm in which 7 patients were on oxihumate at a dose of either 2 g, 4 g or 6 g per day and another arm with 2 patients on placebo. The patients were treated for 2 weeks and followed-up two weeks after completion of treatment.

Clinical Evaluation

None of the patients had previous AIDS-defining events and no such events took place during the study. All of the patients suffered from previous HIV-related infections, but two weeks of treatment was too short a period to reach any meaningful conclusions.

Figure 19:
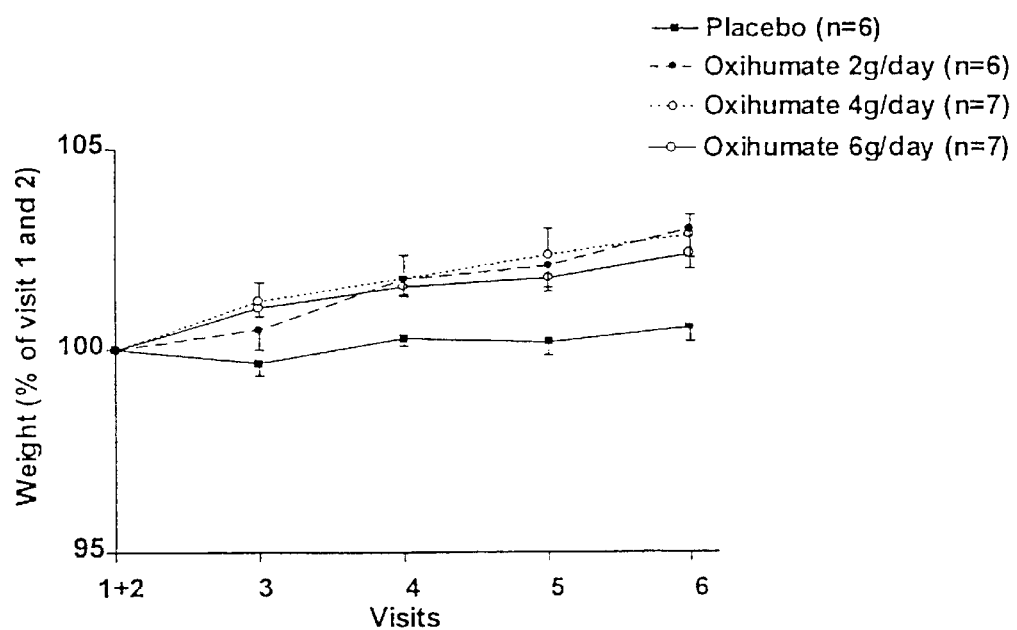
FIG. 19 is a graph showing the weights of HIV-positive patients on a two-week treatment of placebo, 2 g, 4 g, or 6 g oxihumate, measured every five days and expressed as a percentage of their average weight before treatment.

There was a significant increase in the weight of the patients on all three dosages of oxihumate compared to the placebo controls during the study period (FIG. 19).

Most of the oxihumate-treated patients reported a significant improvement in energy levels.

The patients did not experience any gastrointestinal side-effects such as nausea and vomiting while on treatment. Most of the patients reported increased appetite.

Toxicity

Figure 20:
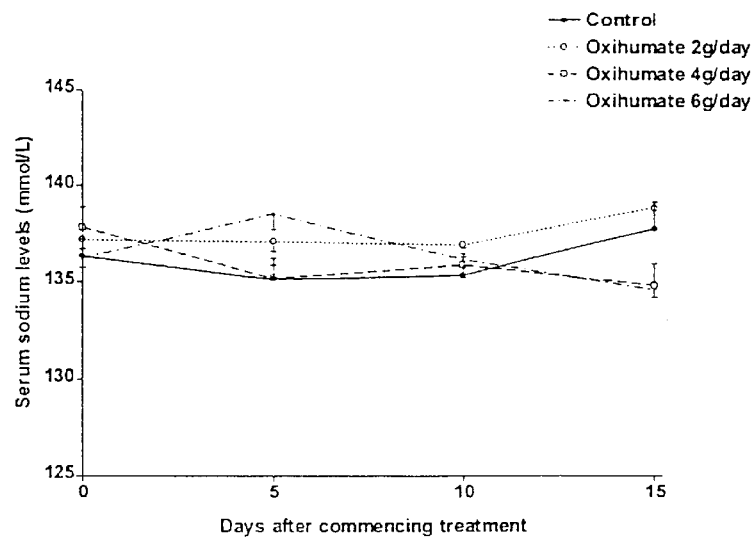
FIG. 20 comprises two graphs illustrating the effect of a two-week treatment of HIV-positive individuals with oxihumate on serum sodium and potassium levels.
Figure 20:
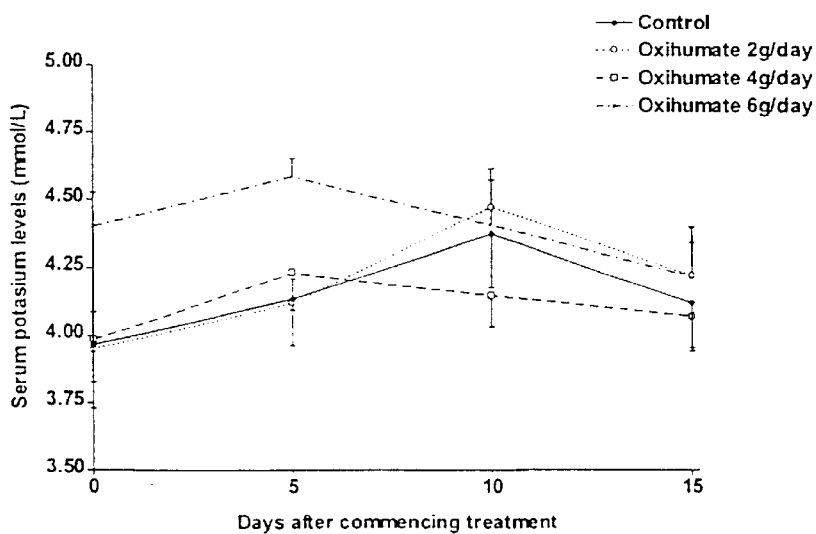
Figure 21:
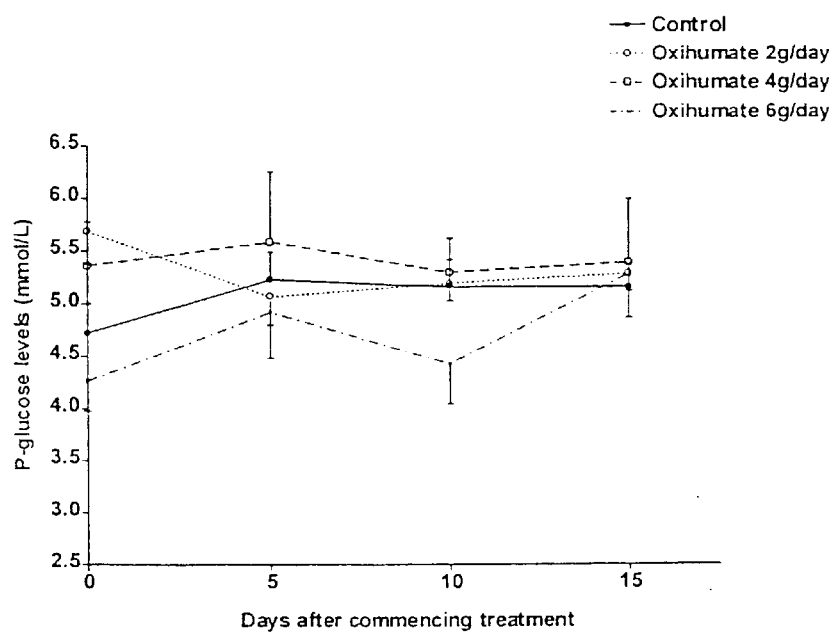
FIG. 21 is a graph showing the effect of a two-week treatment of HIV-positive individuals with oxihumate on plasma glucose levels.
Figure 22:
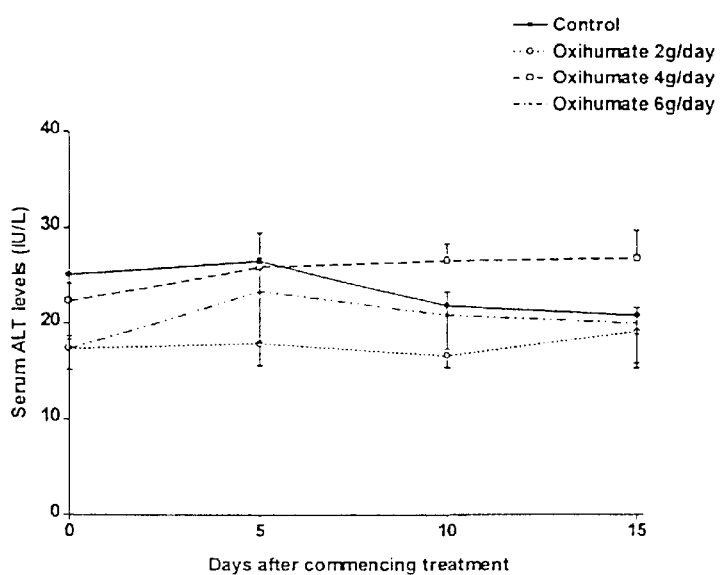
FIG. 22 comprises two graphs illustrating the effect of a two-week treatment of HIV-positive individuals with oxihumate on serum L-alanine transferase and aspertate amino transferase levels.
Figure 22:
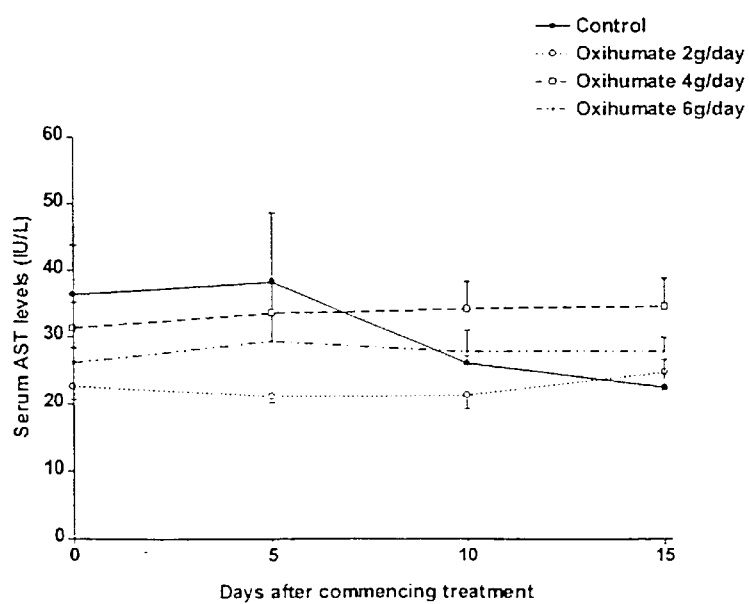
Figure 23:
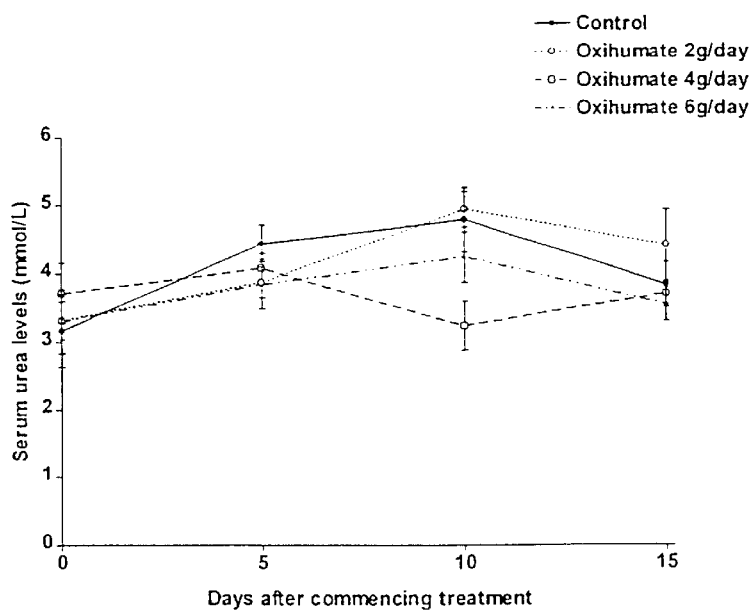
FIG. 23 shows two graphs illustrating the effect of a two-week treatment of HIV-positive individuals with oxihumate on serum urea and creatinine levels.
Figure 23:
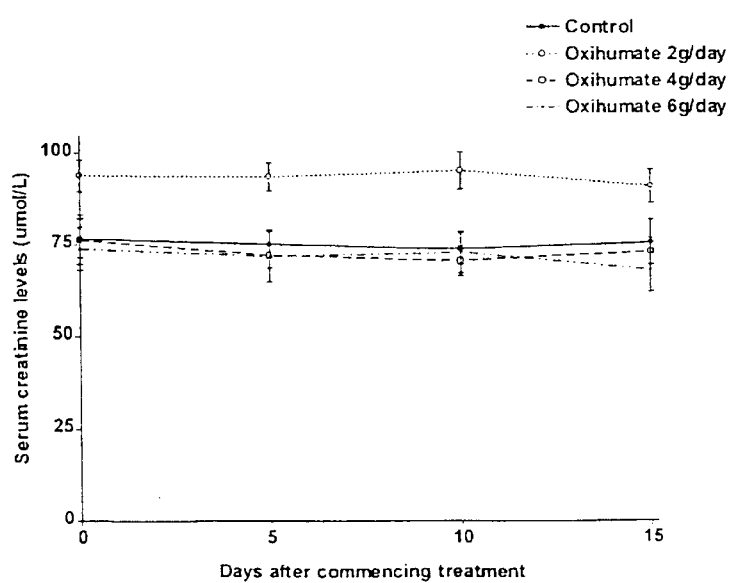
Figure 24:
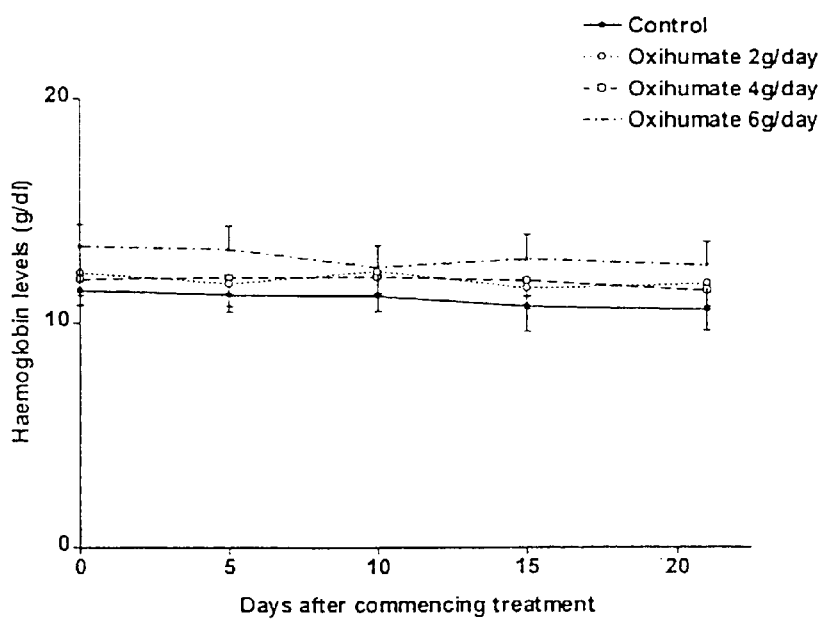
FIG. 24 is a graph showing the effect of a two-week treatment of HIV-positive individuals with oxihumate on hemoglobin levels.
Figure 25:
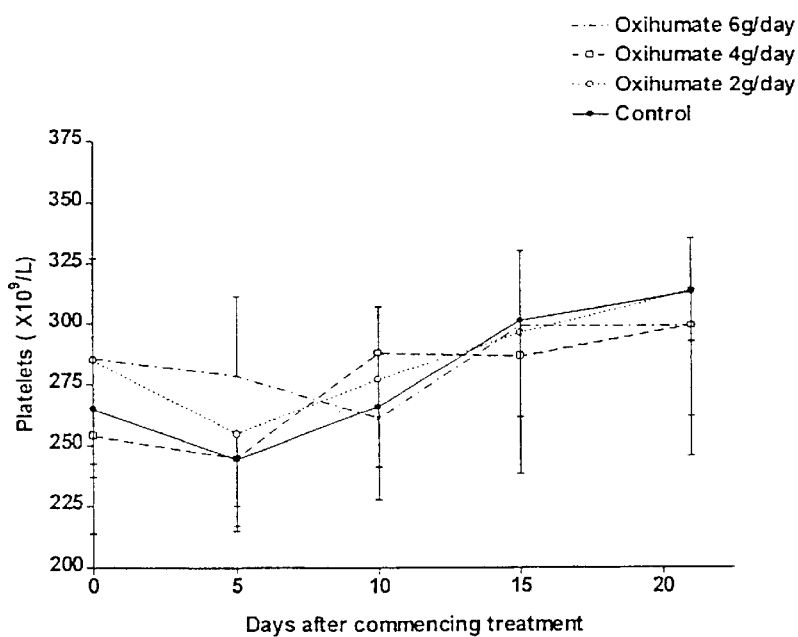
FIG. 25 is a graph showing the effect of a two-week treatment of HIV-positive individuals with oxihumate on platelet counts.
Figure 26:
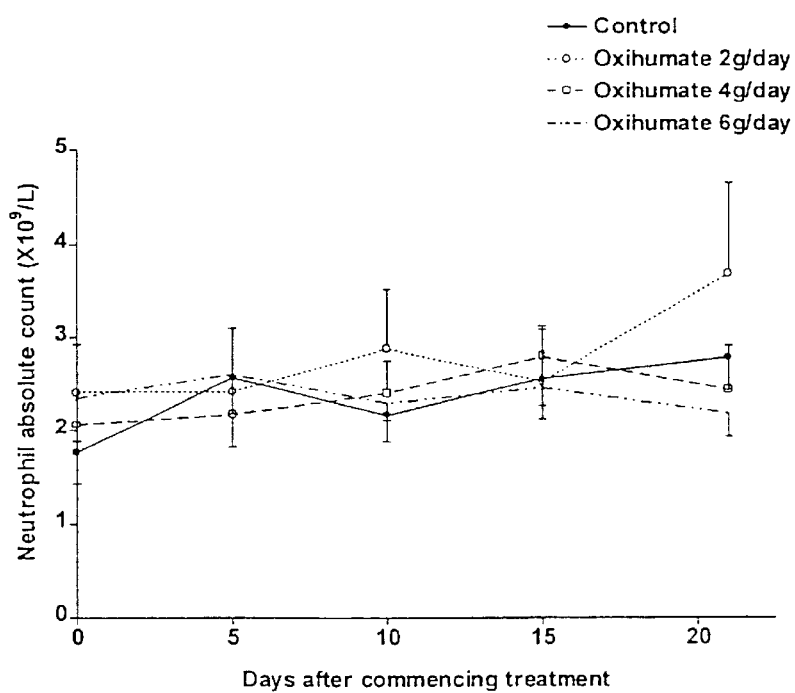
FIG. 26 is a graph showing the effect of a two-week treatment of HIV-positive individuals with oxihumate on absolute neutrophil counts.

There was no change in electrolytes (FIG. 20) or glucose (FIG. 21). No toxicity regarding liver (FIG. 22) and kidney (FIG. 23) function was observed. Haemoglobin levels (FIG. 24) and platelet counts (FIG. 25) remained stable. The absolute neutrophil count (FIG. 26) did, in some cases (2 g/day), increase without any sign of infection being the cause, although the rise was not significant.

Viral Load and $CD_4$ Counts

Figure 27:
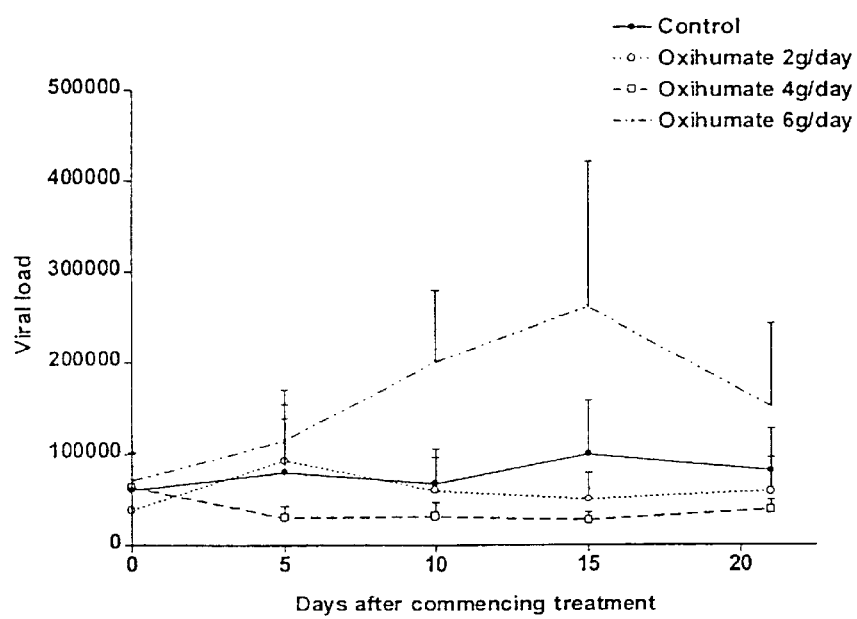
FIG. 27 is a graph showing the effect of a two-week treatment of HIV-positive individuals with oxihumate on viral load.
Figure 28:
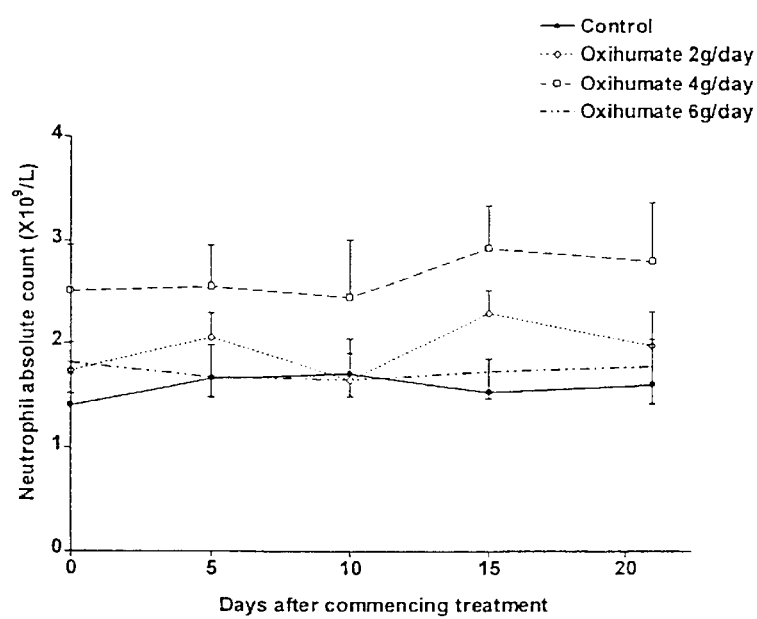
FIG. 28 is a graph showing the effect of a two-week treatment of HIV-positive individuals with oxihumate on absolute lymphocyte counts.
Figure 29:
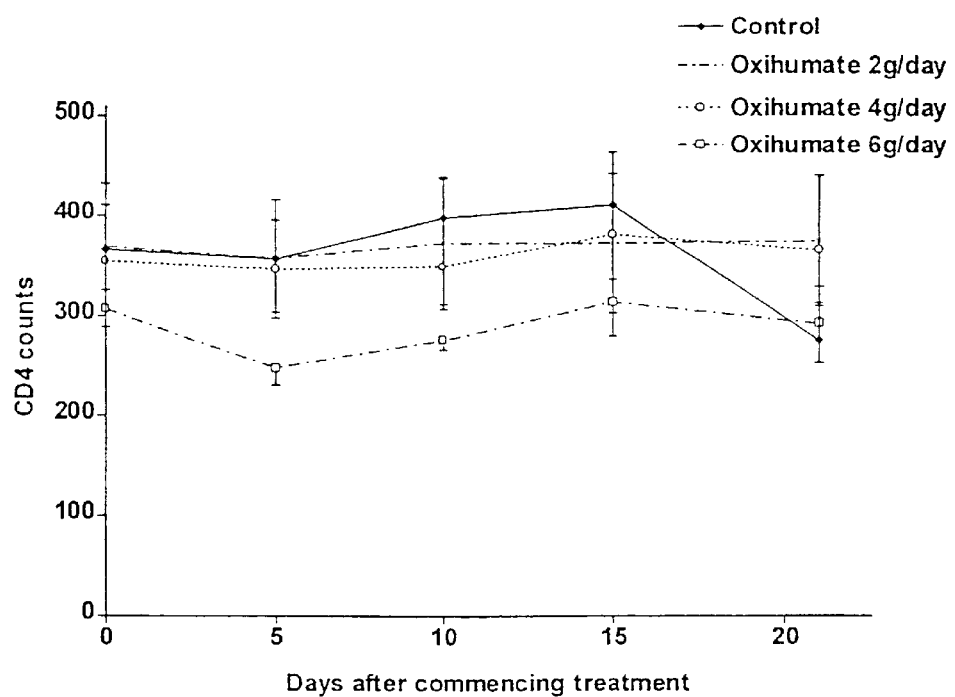
FIG. 29 is a graph showing the effect of a two-week treatment of HIV-positive individuals with oxihumate on CD4 counts.

No significant changes in the viral load (FIG. 27), the absolute lymphocyte count (FIG. 28) and the $CD_4$ count (FIG. 29) were noted.

Conclusion

On a dosage of 2 g, 4 g and 6 g oxihumate per day for two weeks there was no obvious toxicity, while no significant changes in any of the markers reflecting the function of the immune system were noted.

Figure 30:
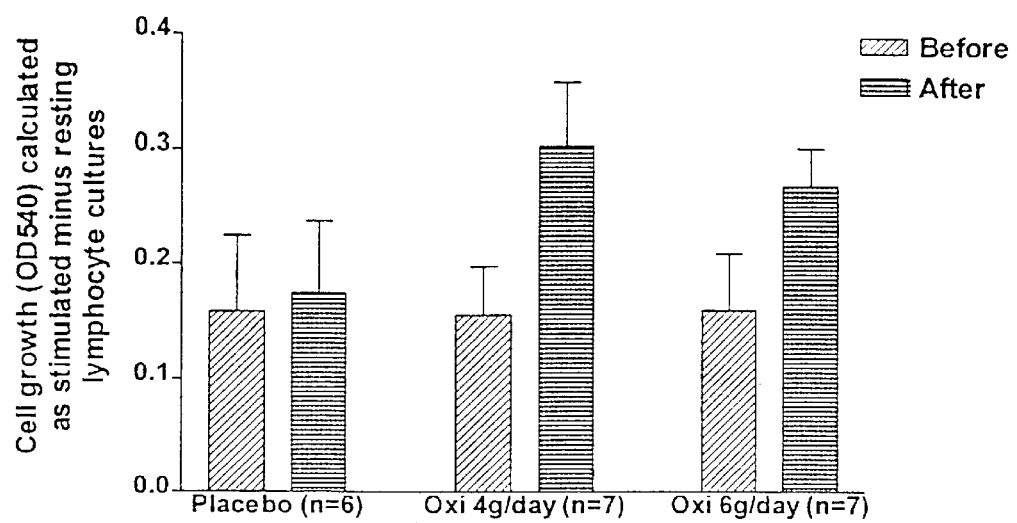
FIG. 30 is a graph showing the effects of a two-week treatment of HIV-positive individuals with oxihumate on PHA-stimulated lymphocyte transformation in vitro.

Effects of a 2-week Treatment of HIV-positive Patients with Oxihumate (at 4 g and 6 g a day) on the Proliferative Response of Phytohaemagglutinin (PHA)(5 mg/ml)-stimulated Human Lymphocytes Oxihumate treatment in vivo increased the proliferative response in vitro of PHA-stimulated lymphocytes (FIG. 30).

xiv) Pharmacokinetics

The pharmacokinetics of $^{123}$I-oxihumate in the baboon was studied by Prof I Dormehl at the Atomic Energy Corporation Institute for Life Sciences (Table 2). Eight baboons were fasted for 24 hours. Four received a mixture of cold and $^{123}$I-labelled oxihumate (55 mg/kg) via a stomach tube directly into the stomach and four received the substance endoscopically directly into the duodenum. Scans were performed and urine and blood samples were taken regularly. The results of these investigations are shown in Table 2.

Rapid systemic uptake of oxihumate was seen within 30 min., occurring faster in the duodenum than in the stomach. The labelled substance appeared in the cardiac bloodpool at 30 min and a maximum of 11.7% of the activity remains at 23 hours. The target organs of $^{123}$I-oxihumate accumulation were the gastro-intestinal tract, liver, kidneys, mucosa and lymphocytes and excretion was via the bowel and kidneys. No side effects were detected during the study.

TABLE 2

The pharmacokinetics of oxihumic acid labelled with $^{123}$I measured as percentage of remaining injected dose in each compartment

| Organ | Arrival Time | T½ | Max Uptake % | T (Max Activity) | Remarks |
|---|---|---|---|---|---|
| Stomach | 0 min | 18 hr > T½ > 5 hr | 100% | | Stomach depo |
| Duodenum | 0 min | 18 hr > T½ > 5 hr | 100% | | Duodenum depo |
| | 30 min | 48 hr > T½ > 5 hr | 55% | 26 hr | |
| Cardiac Bloodpool | 30 min earliest scan | 48 hr > T½ > 24 hr | 11.7% ± 5.1 | 23 hr | Stomach depo |
| Lung | 30 min earliest scan | 28 hr > T½ > 5 hr | 4.13% ± 1.9 | 3 hr | |
| Liver | 3 hr | 48 hr > T½ > 24 hr | 12.8% ± 7.3 | ~20 hr | |
| Kidneys | not visualised - hidden by the intestines | | | | |
| Mucosa | 30 min | 48 hr > T½ > 18 hr | 23% ± 9 | 28 hr | |
| Background | 30 min | 48 hr > T½ > 18 hr | 7.5% ± 4.4 | 24 hr | |
| Thyroid | | | 30% ± 3 | 48 hr | |
| Blood samples | 60 min first sample | | 9.1% ± 2.7 | 23 hr | |
| Lymphnodes | | | 5 | 28 hr | |

% Urinary output (of injected dose)
1–4 hr: 5.71 ± 0.62%
1–5 hr: 12.8 hr ± 3.7%
18–23 hr: 21.43%
23–28 hr: 9.9 ± 2.4%

(xv) Toxicity Studies in Animals

Oxihumate has been tested extensively for toxicity in experimental animals (Table 3). Details of the test and the results thereof are set out hereafter. Further, oxihumate did not produce any measurable toxicity during either acute and sub-chronic oral and dermal exposure.

TABLE 3

Toxicity studies on oxihumate

| STUDY NUMBER | TYPE OF STUDY | RESULTS |
| --- | --- | --- |
| 1503 | Acute oral toxicity in rats | $LD_{50}$ value >3456 mg/kg |
| 1504 | Acute dermal toxicity in rats | $LD_{50}$ value >4147 mg/kg |
| 1505 | Acute dermal irritation | Non-irritant |
| 1506 | Acute eye irritation | Mild irritant |
| 1507 | Skin sensitization | Weak skin sensitizer |
| 1511 | Subchronic oral toxicity in rats (90 day study) | Highest dose tested was 1000 mg/kg/day. No deaths or sick animals. Slight alterations in blood chemistry and slight decreases in body masses. |
| 1557 | Subchronic dermal toxicity in rats (90 day study) | Highest dose tested was 1000 mg/kg/day (of the active substance). No deaths or sick animals. Slight alterations in blood chemistry and slight decreases in body masses. |
| 1633 | Subchronic oral toxicity in dogs (90 day study) | Highest dose tested was 1200 mg/kg/day. No deaths or sick animals. Slight alterations in blood chemistry and slight decrease in body masses. |
| 1639 | Combined chronic toxicity/carcinogenicity study | The chronic toxicity study has been completed. A progress report at the 12 month stage stated that no abnormal clinic signs were observed and none of the animals died or showed any signs of cancer. |

Discussion of Results

Study 1503: Acute Oral Toxicity in Rats

The oral $LD_{50}$ value is estimated to be greater than 3456 mg/kg. Thus, the active ingredient can be classified as practically non-toxic for humans.

Study 1504: Acute Dermal Toxicity Study in Rats

The dermal $LD_{50}$ value to be greater than 4147 mg/kg.

Study 1505: Acute Dermal Irritation/corrosion Test in Rabbits

The evaluation of the Primary Irritation Index (PPI), was made according to both EPA and EEC criteria. No oedema, erythema or notable dermal lesions were observed during the study.

According to EEC criteria oxihumate is classified as a non-irritant for erythema and oedema. Similarly, according to EPA criteria the potassium oxihumate is classified as a non-irritant.

Study 1506: Acute Eye Irritation/corrosion Test in Rabbits

Under the conditions of this study the oxihumate is considered to be a mild irritant to the ocular tissue of the rabbit. According to the EEC Ocular Evaluation Criteria the humate is considered to be non-irritant to the cornea, non-irritant for iris lesion, non-irritant for conjunctival redness and non-irritant for conjunctival oedema.

Study 1507: Contact Hypersensitivity in Albino Guinea Pigs (Magnusson Kligman Maximization Test)

No oedema or erythema was observed in any of the animals during the observation period. It can therefore be concluded that the pure test item did not provoke skin sensitization in the animals. It is therefore classified as having a weak sensitization potential according to the Magnusson Kligman Maximization criteria.

Study 1511: Subchronic Oral Toxicity—Rodent: 90 Day Study with Potassium Oxihumate "None of the animals died during the 90 day study period as a result of the test substance. There were no notable differences between the pathology and organ masses of animals receiving the test substance, compared to the control animals. No abnormal clinical signs were observed in animals receiving the test substance. The only notable changes were the consistent increase in serum globulins as well as a drug-related increase in the size and haemoglobinization of the red blood cells of treated animals. There were also a decrease in serum inorganic phosphate and a decline in circulating lymphocytes. The observed effects were principally evident in female rats. There was a statistically significant decrease in end body mass of male treated animals of the two high-dose groups. The end body masses of these two groups were, however, still within the reference range for animals of that age group.

The observations of the blood chemistry do not necessarily indicate deleterious effects, and might even signify beneficial properties, which should be further researched. Animals in the high-dose group received oxihumate at a dose rate of 1000 mg/kg/day over a 90-day study period. Taking into account the high dose rate, it can be assumed that oxihumate is practically non-toxic over this exposure period at this specific dose.

Study 1557: Subchronic Dermal Toxicity—Rodent: 90 Day Limit Study with Potassium Oxihumate.

Animals received potassium oxihumate at a dose rate of 1000 mg/kg/day over a 90-day period. None of the animals showed any abnormal clinical signs or died during the 90-day study period. There were no differences between the measured pathology, body masses and organ masses of animals receiving the test substance compared to the control animals. The test substance altered some of the chemical pathology parameters. The results were, however, not consistent. The results suggest a very low grade acid-base disturbance.

The test substance, at the dose used and in the manner applied, does not appear to have any serious deleterious effect on the experimental animals as indicated by the parameters assessed.

Study 1633: Potassium Oxihumate Sub-chronic Oral Toxicity Study in Dogs

The test substance, even at 1200 mg/kg/day, did not induce marked clinical signs of toxicity. During the whole study period, all the animals displayed normal physical appearances and behaviour patterns.

The clinical pathological data showed that the test substance had some, but usually small, effects on the measured parameters. Most of the changes were not consistently dose-related and probably not of clinical significance. Many of the changes were to be expected with ageing animals.

All animals were euthanased after the 90-day period and a comprehensive post mortem examination, as well as a histopathological evaluation of an extensive list of organs, was performed. This investigation showed that the test substance did not induce any measurable pathology at the macroscopic and microscopic level. This finding correlates with the clinical pathological investigation.

Oxihumate appears to be a substance of low toxicity in the manner and dose applied.

The results of this study were comparable with the rodent sub-chronic toxicity study.

Study 1639: Combined Chronic Toxicity/carcinogenicity Study. (Progress Report at the Twelve Month Stage)

For the first twelve months of both studies, no abnormal signs were observed in any of the animals dosed with the test substance. None of the animals have died as a result of the test substance and none of the animals are showing any sign of cancer at this stage.

Oxihumate is Therefore a Compound That
  i) increases lymphocyte proliferation. This property is shared by synthetic humic acids;
  ii) exhibits antiviral activity against enveloped viruses, such as HIV-1 and HSV-1;
  iii) increases IL-2 production by stimulated lymphocytes in vitro, a cytokine that might rescue the steadily declining CD 4 lymphocyte population in HIV-infected patients;
  iv) increases IL-4 and IL-6 production by stimulated lymphocytes in vitro, cytokines associated with humoral immunity;
  v) increases antibody production against Newcastle disease in chickens;
  vi) inhibits the secretion of IL-10 by stimulated lymphocytes in vitro, a cytokine associated with a decrease in IL-2 production;
  vii) increases the cytotoxic activity of both resting and PHA-stimulated lymphocytes, using a human liver cancer cell as the target;
  viii) increases both $T_H1$ and $T_H2$ lymphocyte activity in vitro, important host defence mechanisms operative against viral and bacterial infections;
  ix) increases secretion of LTB4 by stimulated lymphocytes, a compound associated with an increase in the production of cytokines associated with both $T_H1$ and $T_H2$ as well as enhanced cytotoxic activity of lymphocytes;
  x) decreases PGE2 secretion by stimulated lymphocytes, a compound associated with inflammation, pain and fever;
  xi) decreases secretion of TNF by stimulated lymphocytes, a compound associated with inflammation;
  xii) inhibits expression of adhesion molecules such as CR3 on cell surfaces;
  xiii) decreases CD38 levels in vitro, a strong negative prognostic marker in HIV-infected individuals;
  xiv) is taken up rapidly and appears in the serum within 30 minutes;
  xv) has very low toxicity in experimental animals;
  xvi) is non-toxic up to a dosage of 6 g per day in HIV-infected individuals;
  xvii) increases the lymphoproliferative response and weight of HIV-infected individuals after two weeks.

REFERENCES

Adamek W. Introductory report on oncostatic and therapeutic nature of the peat preparation in human neoplastic disease. In: Peat and Peatlands in the Natural Envirnoment Protection. Proc 5$^{th}$ Int Congress, Poznam, Poland 1976:1:417–429.
Aspinal S, Bos P, Alexander J J. Oral administration of Efamol G to nude mice bearing human hepatocellular carcinoma zenografts. *S A J Science* 1988:84:852–854.
Bennet L R, Connon F E. Effects of lytic agents on plasma membranes of Ehrlich ascites-tumor cells and mouse erythrocytes. *J Nat Cancer Inst* 1957; 19:999–1011.
Bergh J J, Cronje I J, Dekker J. Dekker T G, Gerritsma L M, Mienie L J. Non-catalytic oxidation of water-slurried coal with oxygen: identification of fulvic acids and acute toxicity. *Fuel* 1997;76:149–154.
Bernacchi F, Ponzanelli l. Barale R. Loprieno N. Mutagenic activity of coal-derived humic compounds evaluated by the Ames test. *Mutation Research* 1996;369:107–112.
Bofill M, Mocroft A, Lipman M, Medina E, Borthwick N J, Sabin C A, Timus A, Winter M, Baptista L, Johnson M A, Lee C A, Phillips A N. Janossy G. Increased numbers of primed activated CD8$^+$CD38$^+$CD45RO$^+$T cells predict the decline of CD4$^+$ T cells in HIV-1-infected patients. AIDS 1996;10:827–834.
Brandt H. Die Behandlung degenerativer Erkrakungen der Wirbelsäule und der Gelenke mit salizylierten Huminsaurebädern. *Fortschr Med* 1964:82:110.
Cloete T E, Swart H, Cronje I J. Dekker J. Oxidized coal products as industrial bactericides. Third International Symposium on Gas, Oil, Coal and Environmental Biotechnology. Dec. 3–5, 1990. New Orleans, Louisiana.
Davies G. Properties and Functions of Humic Acids. Meeting Report. The Nucleus Febr. 1996, p 17.
Eichelsdörfer D. Moor in der Heilkunde. In: Moor- und Torfkunde. Ed K Göttlich, Schweizerbart, Stuttgart, 1976.
Gramsch H. Ein Beitrag zur Behandlung der Gastropathien. *Med Monatsschr.* 1961;15:658–687.
Haanel B F. Facts about peat, Mines Branch Publ No 614, Can Dept Mines, Ottawa, 1924.
Klöcking R, Sprössig M, Wutzler P. Thiel K D, Helbig B. Antiviral wirksam Huminsäureähnliche Polymere. *Z. Physiother.* 1983:33:95–101.
Lopez-Ferandez M F, Blanco-Lopes M J, Castineira M P, Batlle J. Further evidence for recessive inheritance of von Willebrand disease with abnormal binding of von Willebrand factor to factor VIII. *Am J Hematol* 1992:40:20–27.
Motohisa S, Yoshinori H, Shuzo K. Humic acids for treatment of skin disorders. In: C A 80, 1974, p 283 100222u. Patent Japan. Kokai 7392, 524.
Reichert B. Huminsäuren und ihre Derivate in der modernen Therapic. *Dtsch Apoth* 1966;18:204–206.
Salz H. Salhumin-Gel, ein Lokaltherapeutikum mit hyperämisierender, entzündungshemmender und analgetischer Wirkung. *Med Monatsschr* 1974;28:548–550.
Sato T, Ose Y, Nagase H. Desmutagenic effect of humic acid. *Mutation Research* 1986;162: 173–178.
Schneider J, Weis R, Manner C. Kary B, Werner A, Seubert B J, Riede U N. Inhibition of HIV-1 in cell culture by synthetic humate analogues derived from hydroquinone: mechanism of inhibition. *Virology* 1996;218:389–395.
Thiel K D, Klöcking R, Schweizer H, Sprössig M. Untersuchungen in vitro zur antiviralen Aktivität von Ammoniumhumat gegenüber Herpes simplex-Virus Typ 1 und Typ 2, Zentralbl. Bakteriol. Parasiten k d, Infection skr Hyg Abt 1 1977:239:301–321.
Visser S A. Some biological effects of humic acids in the rat. *Acta Biol Med Germ* 1973;31:569–581.
Visser S A. Surface active phenomena by humic substances of aquatic origin. *Rev Fr Sci Eau* 1982;1:285–295.
Zsindely A, Hofmann R, Klöckina R. Über den Einfluss oral applizierter Huminsäuren auf den Nukleinsäurestoffwechsel von Ascites-rumorzellen bei M äusen. *Acta Bio. Debrecina* 1971;9:71–77.

What is claimed is:

1. A method of stimulating lymphocytes in a subject, which method comprises the step of administering to the subject an oxihumic acid, salt, or ester having the following functional group analysis:
  Total acid groups: 3–13 meq/g;
  Carboxylic groups: 0.5–12 meq/g; and
  Phenolic groups: 0.5–9 meq/g.

2. The method of claim 1, wherein the lymphocytes are $T_H1$ and $T_H2$ lymphocytes.

3. A method of treating inflammation, pain, or fever, or combinations thereof in a subject comprising the step of administering to the subject an oxihumic acid, salt, or ester having the following functional group analysis:

Total acid groups: 3–13 meq/g;

Carboxylic groups: 0.5–12 meq/g; and

Phenolic groups: 0.5–9 meq/g.

4. The method according to claim 1, wherein the administration is oral.

5. The method according to claim 1, wherein the subject is a human, animal, or bird.

6. The method according to claim 3, wherein the administration is oral.

7. The method according to claim 3, wherein the subject is a human, animal, or bird.

8. A method of stimulating lymphocytes in a subject, which method comprises the step of administering to the subject a coal-derived oxihumic acid, salt, or ester having the following functional group analysis:

Total acid groups: 3–13 meq/g;

Carboxylic groups: 0.5–12 meq/g; and

Phenolic groups: 0.5–9 meq/g.

9. A method of treating inflammation, pain, or fever, or combinations thereof in a subject comprising the step of administering to the subject a coal-derived oxihumic acid, salt, or ester having the following functional group analysis:

Total acid groups: 3–13 meq/g;

Carboxylic groups: 0.5–12 meq/g; and

Phenolic groups: 0.5–9 meq/g.

\* \* \* \* \*